(12) United States Patent
Robert et al.

(10) Patent No.: US 7,726,311 B2
(45) Date of Patent: Jun. 1, 2010

(54) METHOD AND APPARATUS FOR CONDUCTING TOTAL LIQUID VENTILATION WITH CONTROL OF RESIDUAL VOLUME AND VENTILATION CYCLE PROFILE

(75) Inventors: Raymond Robert, Sherbrooke (CA);
Stéphane Cyr, Sherbrooke (CA);
Philippe Micheau, Rock Forest (CA);
Hervé Walti, Sherbrooke (CA);
Jean-Paul Praud, Sherbrooke (CA)

(73) Assignee: Universite De Sherbrooke, Montreal, Quebec (CA)

( * ) Notice: Subject to any disclaimer, the term of this patent is extended or adjusted under 35 U.S.C. 154(b) by 1781 days.

(21) Appl. No.: 10/724,294

(22) Filed: Nov. 28, 2003

(65) Prior Publication Data
US 2004/0134486 A1 Jul. 15, 2004

(30) Foreign Application Priority Data
Nov. 29, 2002 (CA) .................................. 2413041

(51) Int. Cl.
*A61M 16/00* (2006.01)
*F16K 31/02* (2006.01)
(52) U.S. Cl. .......................... 128/205.19; 128/204.21; 128/205.18
(58) Field of Classification Search .......... 128/200.24, 128/203.14, 203.17, 203.24, 203.26, 203.27, 128/204.17, 204.21, 205.18, 205.19, 205.24; 60/529, 532
See application file for complete search history.

(56) References Cited
U.S. PATENT DOCUMENTS
4,067,696 A * 1/1978 Curtis ......................... 422/47

4,206,754 A * 6/1980 Cox et al. .............. 128/204.21

(Continued)

FOREIGN PATENT DOCUMENTS
CA          2035492          3/2001

(Continued)

OTHER PUBLICATIONS

Hirschl et al. "Evaluation of gas exchange, pulmonary compliance, and lung injury during total and partial liquid ventilation in the acute respiratory distress syndrome," *Critical Care Med.* 24, (1996), pp. 1001-1008 [15 sheets].

(Continued)

*Primary Examiner*—Justine R Yu
*Assistant Examiner*—Kristen C Matter
(74) *Attorney, Agent, or Firm*—Fay Kaplun & Marcin, LLP

(57) ABSTRACT

A method of applying total liquid ventilation to a patient according to a ventilation cycle including inspiration and expiration profiles, comprises supplying oxygenated liquid to the patient's lungs, withdrawing liquid from the patient's lungs, and controlling independently supply of oxygenated liquid to the patient's lungs and withdrawal of liquid from the patient's lungs. This supply and withdrawal independent control comprises producing a ventilation cycle having independently controlled inspiration and expiration profiles. To carry out the method, a total liquid ventilator system comprises an inspiration pump for supplying oxygenated liquid to the patient's lungs, and an expiration pump for withdrawing liquid from the patient's lungs. A ventilation cycle control comprises first and second pump controllers connected to the inspiration and expiration pumps, respectively, to produce a ventilation cycle having independently controlled inspiration and expiration profiles.

10 Claims, 13 Drawing Sheets

U.S. PATENT DOCUMENTS

| | | | | |
|---|---|---|---|---|
| 4,232,665 | A | | 11/1980 | Vaseen |
| 4,598,706 | A | * | 7/1986 | Darowski et al. ...... 128/205.24 |
| 4,758,431 | A | | 7/1988 | Osterholm |
| 5,092,326 | A | * | 3/1992 | Winn et al. ............ 128/205.13 |
| 5,158,536 | A | | 10/1992 | Sekins et al. |
| 5,226,727 | A | | 7/1993 | Reichner |
| 5,335,650 | A | * | 8/1994 | Shaffer et al. .......... 128/200.24 |
| 5,437,272 | A | | 8/1995 | Fuhrman |
| 5,464,534 | A | * | 11/1995 | Fischel .................. 210/321.68 |
| 5,490,498 | A | | 2/1996 | Faithfull et al. |
| 5,492,109 | A | | 2/1996 | Hirschl et al. |
| 5,531,219 | A | | 7/1996 | Rosenberg |
| 5,540,225 | A | | 7/1996 | Schutt |
| 5,562,608 | A | | 10/1996 | Sekins et al. |
| 5,590,651 | A | | 1/1997 | Shaffer et al. |
| 5,655,521 | A | | 8/1997 | Faithfull et al. |
| 5,664,563 | A | * | 9/1997 | Schroeder et al. ...... 128/204.25 |
| 5,694,924 | A | * | 12/1997 | Cewers .................. 128/204.21 |
| 5,704,346 | A | * | 1/1998 | Inoue .................... 128/204.24 |
| 5,706,830 | A | * | 1/1998 | Parker .................... 128/203.12 |
| 5,707,352 | A | | 1/1998 | Sekins et al. |
| 5,788,665 | A | | 8/1998 | Sekins |
| 5,850,835 | A | * | 12/1998 | Takaki et al. ........... 128/204.18 |
| 5,853,003 | A | | 12/1998 | Faithfull et al. |
| 5,937,853 | A | * | 8/1999 | Strom .................... 128/204.23 |
| 6,041,777 | A | | 3/2000 | Faithfull et al. |
| 6,105,572 | A | | 8/2000 | Shaffer et al. |
| 6,166,092 | A | | 12/2000 | Sekins et al. |
| 6,241,945 | B1 | | 6/2001 | Owen |
| 6,346,552 | B1 | * | 2/2002 | Albrecht ..................... 514/771 |
| 6,571,796 | B2 | * | 6/2003 | Banner et al. .......... 128/204.26 |
| 6,691,705 | B2 | * | 2/2004 | Dittmann et al. ....... 128/203.25 |
| 6,694,977 | B1 | * | 2/2004 | Federowicz et al. .... 128/204.18 |
| 6,983,749 | B2 | * | 1/2006 | Kumar et al. .......... 128/204.15 |
| 2002/0104537 | A1 | * | 8/2002 | Banner et al. .......... 128/204.25 |

FOREIGN PATENT DOCUMENTS

| | | |
|---|---|---|
| ES | 2 154 596 | 4/2001 |
| WO | WO 91/03267 | 3/1991 |
| WO | WO 92/19232 | 11/1992 |
| WO | WO 93/09833 | 5/1993 |
| WO | WO 94/08652 | 4/1994 |
| WO | WO 97/19719 | 6/1997 |
| WO | WO 97/32621 | 9/1997 |
| WO | WO 99/24100 | 5/1999 |
| WO | WO 99/52621 | 10/1999 |
| WO | WO 99/62626 | 12/1999 |

OTHER PUBLICATIONS

Pedneault et al. "Total liquid ventilation using a modified extracorporeal gas exchange circuit: preliminary results in lambs," [abstract], *Pediatr Pulmonol Suppl.* 18, (1999), p. A241.

Hirschl et al. "Liquid ventilation in adults, children and full-term neonates," *The Lancet.* 346, (1995), pp. 1201-1202 [4 sheets].

Shaffer et al. "The effects of liquid ventilation on cardiopulmonary function in preterm lambs," *Pediatr Res* 17, (1983), pp. 303-306.

Wolfson et al. "Comparison of gas and liquid ventilation: clinical, physiological, and histological correlates," *J Appl Physiol.* 72, (1992), pp. 1024-1031.

Clark et al. "Survival of mammals breathing organic liquids equilibrated with oxygen at atmospheric pressure," *Science*, 152, (1966) pp. 1755-1756.

Wolfson et al. "Liquid-assisted ventilation: an alternative respiratory modality," *Pediatr Pulmonol.* 26, (1998), pp. 42-63.

Wolfson et al. "Pulmonary administration of vasoactive substances by perfluorochemical ventilation," *Pediatrics.* 97, (1996) pp. 449-455 [13 sheets].

Sekins et al. "Recent innovations in total liquid ventilation system and component design," *Biomed Instrum Technol.* 33, (1999), pp. 277-284.

Larrabe et al. "Development of a time-cycled volume-controlled Pressure-limited respirator and lung mechanics system for total liquid ventilation," *IEEE Transactions on Biomedical Engineering.* 48, (2001), pp. 1134-1144.

Wolfson et al. "Multifactorial analysis of exchanger efficiency and liquid conservation during perfluorochemical liquid-assisted ventilation". *Biomed Instrum Technol.* 33, (1999), pp. 260-267.

Shaffer et al. "Perfluorochemical liquid as a respiratory medium," *Art Cells Blood Subs Immob Biotech 22*, (1994), pp. 315-326 [abstract only] [2 sheets].

Fuhrman et al. "Perfluorocarbon-associated gas exchange," *Critical Care Med.* vol. 19, No. 5, (1991), pp. 712-722.

Philips et al. "On-line techniques for perfluorochemical vapor sampling and measurement," *Biomed Instrum Technol.* 33, (1999), pp. 348-355.

Libros et al. "A perfluorochemical loss/restoration (l/r) system for tidal liquid ventilation," *Biomed Instrum Technol.* 34, (2000), pp. 351-360.

Leach et al. "Partial liquid ventilation with perflubron in premature infants with severe respiratory distress syndrome," *The New England J of Med*, vol. 335(11), (1996) pp. 761-767 [15 sheets].

Hirschl et al. "Development and application of a simplified liquid ventilator," *Critical Care Med.* vol. 23(1), (1995) pp. 157-163 [9 sheets].

Meinhardt et al. "Development and application of a double-piston configured, total-liquid ventilatory support device," *Critical Care Med.* vol. 28(5), (2000) pp. 1483-1488 [11 sheets].

Heckman et al. "Software for real-time control of a tidal liquid ventilator," *Biomed Instrum Technol.* 33, (1999) pp. 268-276.

Cox et al. "Liquid ventilation a comprehensive overview," *Neonatal Network* vol. 15, No. 3, (1996) pp. 31-43.

Degraeuwe et al. "A feedback controller for the maintenance of FRC during tidal liquid ventilatory: theory, implementation, and testing," *The Int'l J of Artificial Organs*, vol. 23, No. 10, (2000) pp. 680-688.

\* cited by examiner

METHOD AND APPARATUS FOR CONDUCTING TOTAL LIQUID VENTILATION WITH CONTROL OF RESIDUAL VOLUME AND VENTILATION CYCLE PROFILE

FIELD OF THE INVENTION

The present invention relates to a method and apparatus for conducting total liquid ventilations of patients treated for respiratory difficulties.

BACKGROUND OF THE INVENTION

Three to five percent of newborns in intensive care units are afflicted with a respiratory distress that makes them refractory to optimal ventilation by artificial means. Inflammation of the lungs is even aggravated by conventional artificial ventilation. Insufficient oxygenation of arterial blood and internal organs, particularly of the brain, results from such conditions. A promising alternative in the treatment of acute respiratory distress syndrome (ARDS) is liquid ventilation using breathable inert liquids. The advantages of this technique are suggested by theoretical considerations and supported by solid experimental evidence, which have been well known for many years.

Liquid ventilation can be achieved in two ways, either as partial (PLV) or total liquid ventilation (TLV). PLV uses a conventional gas ventilator after the lungs have been partially filled with perfluorocarbon (PFC) liquid. This technique requires no special ventilator and has been the subject of clinical studies for many years. However, it is clear that the benefits of liquid ventilation are best achieved by total liquid ventilation, wherein the lungs are completely filled with breathable inert liquid oxygenated by external means. Furthermore, the idea of re-establishing prenatal conditions in diseased lungs of newborns while healing occurs appears to be intuitively sound [Praud J P. (2000) "Le liquide pulmonaire". In: Dehan M, Micheli J, eds. *Le poumon du nouveau-né*. Paris: Doin, pp 49-51].

The considerable advantage of liquid ventilation over gaseous ventilation in acute respiratory failure is the possibility, as a result of eliminating the air-liquid interface of the lungs, of recruiting and expanding pathologically non-compliant lung alveoli at much lower pressures. The risk of volo/barotrauma is greatly reduced, alveolar ventilation is more uniform, atelectasis is eliminated, and ventilation/perfusion unevenness is decreased. These benefits have been noted in all studies carried out on animal models of newborn respiratory distress [Hirschl R B, Tooley R, Parent A, Johnson K, Bartlett R H. (1996) "Evaluation of gas exchange, pulmonary compliance, and lung injury during total and partial liquid ventilation in the acute respiratory distress syndrome", Crit Care Med 24:1001-8; Pedneault C, Renolleau S, Gosselin R, Letourneau P, Praud J P. (1999) "Total liquid ventilation using a modified extra-corporeal gas exchange circuit: preliminary results in lambs", Pediatr Pulmonol Suppl 18: A241; Hirschl R B et al. (1995) "Liquid ventilation in adults, children and full-term neonates", Lancet 346:1201-2; Shaffer T H, Douglas P R, Lowe C A, Bhutani V K. (1983) "The effects of liquid ventilation on cardiopulmonary function in preterm lambs". *Pediatr Res* 17:303-6; Wolfson M R, Greenspan J S, Deoras K S, Rubenstein S D, Shaffer T H. (1992) "Comparison of gas and liquid ventilation: clinical, physiological, and histological correlates", J Appl Physiol 72:1024-31].

Perfluorocarbons are most often selected as breathable inert liquids. They are non-toxic, chemically stable and biocompatible. In addition, they have been identified as "ideal" liquids for this purpose, since they diffuse rapidly into respiratory airways, have very low surface tension and are very good solvents for respiratory gases allowing them to provide both oxygenation and efficient removal of $CO_2$ [Clark C, Gollan F, (1966) "Survival of mammals breathing organic liquids equilibrated with oxygen at atmospheric pressure, *J Appl Physiol*, 21:1755-6, 1966]. PFCs not only "wash" debris and inflammatory molecules from the patient's airways [Wolfson M R, Greenspan J S, Shaffer, T H. (1998) "Liquid-assisted ventilation: an alternative respiratory modality" Pediatr Pulmonol 26: 42-63] but can also be used for administering locally-applied medicines such as pulmonary artery dilators [Wolfson M R, Greenspan J S, Shaffer T H. (1996) "Pulmonary administration of vasoactive substances by perfluorochemical ventilation", Pediatrics 97:449-55]. A first PFC, perflubron, has been approved for medical use, while others, such as perfluorobutane, are currently being examined by the FDA.

Many types of liquid ventilators have been developed and disclosed in the literature. Generally, clinical studies have been conducted using with systems supplied by gravity, using reservoirs above and below the patients' lungs to bring about inspiration and expiration. A drawback is that this type of system does not enable adequate monitoring and control of all the ventilation parameters.

Research laboratories initially constructed liquid ventilators using costly existing equipments for oxygenation and external circulation. In most of the cases, complex pumping was used, composed of peristaltic pumps, liquid reservoirs and several valves with by-pass systems. A major problem then acknowledged by researchers was to design a user-friendly, simple, efficient, safe and reliable ventilator to bring TLV in an intensive care environment.

In order to decrease the mechanical complexity of liquid ventilators, Hirsch et al. [Hirschl R B, Tooley R, Parent A, Johnson K, Bartlett R H. (1996) "Evaluation of gas exchange, pulmonary compliance, and lung injury during total and partial liquid ventilation in the acute respiratory distress syndrome", Crit Care Med 24:1001-8] developed a connector with a venturi, which allows both inspiration and expiration without using a by-pass circuit and provides continuous liquid flow throughout the system.

Shaffer et al. [Shaffer, Thomas H., Wolfson, Marla R., Heckman, James L., Hoffman, John, (2000), "Liquid Ventilator", U.S. Pat. No. 6,105,572, 14 p] subsequently developed a total liquid ventilator using a roller pump to force PFC liquid through a respiration and regeneration closed-loop circuit. However, this type of pump generates a pulsatile flow, which causes oscillation of pressure measurements. Thus, other recently developed ventilators [Sekins K M, Nugent L, Mazzoni M, Flanagan C, Neer L, Rozenberg A, Hoffman J. (1999) "Recent innovations in total liquid ventilation system and component design" Biomed Instrum Technol 33 :277-84; Larrabe J L., Alvarez F J., Gatiasoro Cuesta E., Valls-i-Solers A., Alfonso L F., Arnaiz A., Fernandez M B., Loureiro B., Publicover N G., Roman L., Casle J A., Gomez M A. (2001), "Development of a time-cycled volume-controlled Pressure-limited respirator and lung mechanics system for total liquid ventilation", IEEE Transactions on Biomedical engineering 48:1134-1144] use a double piston pump, of which one piston is dedicated to inspiration and the other piston to expiration. Both pistons are displaced simultaneously on a single platform.

The gas exchanger is crucial to efficiency of TLV, since it must completely remove $CO_2$ from the PFC liquid and replace it with oxygen before the liquid may be returned to the patient's lungs. And $CO_2$ dissolves more easily than does oxygen in PFC liquid. Therefore, in order to bring about adequate gas exchange, many total liquid ventilators are equipped with a costly external blood oxygenator. This piece of equipment contains a silicone membrane comprised of two walls; the oxygen flows between the two walls of the silicone membrane while the PFC liquid flows on the outside of these walls. A major drawback of this oxygenator is that oils from the silicone are extracted by the PFC liquid, which increases membrane replacement frequency and hence operating cost. In addition, PFC liquid leaks through the silicone membrane to pass into the oxygen stream, resulting in PCF losses and higher operating cost.

In other applications, a combination of an atomizer with a bubbler tube has been developed to replace the membrane oxygenator. The column of this oxygenator consists principally of a long vertical tube into which PFC liquid is sprayed through a nozzle at the top and oxygen is injected at the base through a porous stone. Gas exchange occurs through direct contact between the gas bubbles and the liquid. Efficiency is improved by inserting grids into the column to increase the time of residence of the gas bubbles in the liquid [Sekins K M, Nugent L, Mazzoni M, Flanagan C, Neer L, Rozenberg A, Hoffman J. (1999) "Recent innovations in total liquid ventilation system and component design", Biomed Instrum Technol 33 :277-84.].

However, the performance of the atomizer-bubbler combination is strongly dependent on gas flow rate. When gas flow rate is insufficient, the porous stone does not generate a uniform flow of bubbles. When too high a flow rate is produced, gas bubbles join together to form a cluster of bubbles, which greatly decreases the gas exchange area. In addition, large amounts of liquid are required to fill the column.

As an alternative to oxygenation systems based on membranes or atomizer-bubbler combinations, Lawrence J. NUGENT developed a new type of liquid-breathing gas exchanger described in International Publication WO 99/62626 dated Mar. 16, 2000. This gas exchanger is composed of a fluid-dispersion unit for projecting a thin film of liquid onto a surface exposed to an oxygen gas stream.

The flow of oxygen through the oxygenator is evacuated, carrying with it both $CO_2$ and PFC liquid vapours. During TLV, significant losses of liquid therefore occur. Multifactorial analysis on the efficiency of the exchangers and the conservation of the liquid during TLV has shown that PFC liquid losses are greater in atomizer-bubbler combinations than in membrane-type gas exchangers [Wolfson M R, Miller T F, Peck G, Shaffer T H. (1999) "Multifactorial analysis of exchanger efficiency and liquid conservation during perfluorochemical liquid-assisted ventilation". *Biomed Instrum Technol*. 33 :260-7]. This can be explained largely by an evacuation of atomized PFC liquid outside the oxygenator under the form of small droplets conveyed by the gaseous stream, in addition to evaporation losses.

Losses of PFC liquid must be minimized, both for economic reasons and for the protection of medical equipments not compatible with PFC vapours. To meet with this requirement, a condenser is generally incorporated into the system in order to recover PFC vapours escaping from the oxygenators, without interfering with gas flow.

An alternative to the use of condensers would be to recirculate the gas stream, which could allow practically complete retention of PFC vapours. Faithfull and Shutt [Faithfull and Shunt (1999), "Methods and Apparatus for Closed-Circuit Ventilation Therapy", U.S. Pat. No. 6,041,777, 26 p] have developed a method and an apparatus for this type of system, which allows prolonged administration of PFC liquid without excessive losses due to evaporation. A drawback is that these method and apparatus require a system for extracting $CO_2$ from the closed-loop circuit.

Health-care personnel are aware that a patient may suffer hyper distension of the lungs or collapse of the respiratory airways as well as incomplete gas diffusion. The ventilator must therefore inform the health-care personnel about the patient's status by means of measurements such as compliance, respiratory airways pressure, lung volume, etc. To meet with this requirement, Shaffer et al. [Shaffer T H, Wolfson M R, Greenspan J S, Rubenstein S D, Stern R G. (1994) "Perfluorochemical liquid as a respiratory medium", Art Cells Blood Subs Immob Biotech 22:315-326] developed a monitoring process for liquid ventilators, based on a comparison of current conditions with a range of desired values, in order to activate alarms or servo-valves on the network of conduits.

Nevertheless, the problem is more complex than simply determining when to activate an alarm. A continuous measurement of the volume of liquid in the lungs is highly desirable, rather than relying on pressure measurement to indicate errors between the volume of liquid injected into and the volume withdrawn from the lungs. Such errors, even small, could result in decreased or increased residual liquid volume in the lungs on the long term. There is currently no efficient method for continuous measurement of such volume of liquid; for example, measurement of a variation in the patient's weight does not constitute a practical method for implementation in the intensive care units.

SUMMARY OF THE INVENTION

The present invention relates to a method of applying total liquid ventilation to a patient according to a ventilation cycle including inspiration and expiration profiles, comprising supplying oxygenated liquid to the lungs of the patient, withdrawing liquid from the patient's lungs, and controlling independently supply of oxygenated liquid to the patient's lungs and withdrawal of liquid from the patient's lungs. The supply and withdrawal independent control comprises producing a ventilation cycle having independently controlled inspiration and expiration profiles.

The present invention is also concerned with a system for applying total liquid ventilation to a patient according to a ventilation cycle including inspiration and expiration profiles, comprising an inspiration pump for supplying oxygenated liquid to the lungs of the patient, an expiration pump for withdrawing liquid from the patient's lungs, and a ventilation cycle control means comprising first and second pump controllers connected to the inspiration and expiration pumps, respectively, to control independently these inspiration and expiration pumps in order to produce a ventilation cycle having independently controlled inspiration and expiration profiles.

The foregoing and other objects, advantages and features of the present invention will become more apparent upon reading of the following non-restrictive description of an illustrative embodiment thereof, given as example only with reference to the appended drawings.

BRIEF DESCRIPTION OF THE DRAWINGS

In the appended drawings:

FIG. 8b is a side elevational view (panel removed) showing one example of the gas flow path through the condenser module of FIG. 8a;

DETAILED DESCRIPTION OF THE ILLUSTRATIVE EMBODIMENT

Figure 1:
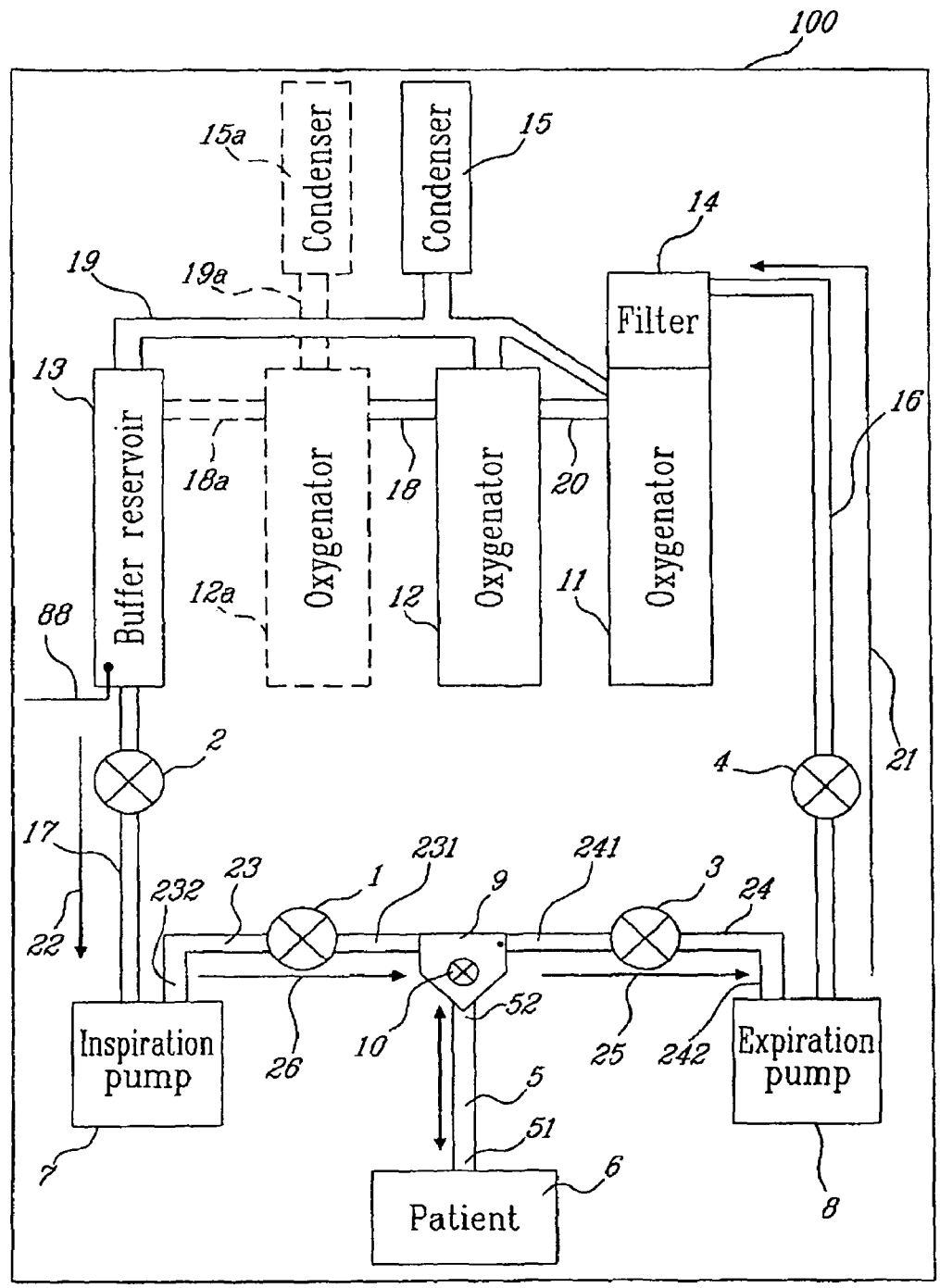
FIG. 1 is a schematic diagram of a liquid circuit of the non-restrictive illustrative embodiment of the system according to the present invention for conducting total liquid ventilation.

A major objective of the illustrative embodiment of the present invention is to provide a total liquid ventilator system that is not only user friendly but also sufficiently efficient, safe and reliable for bringing TLV into intensive care units. This implies development and integration of numerous components, including pump(s), oxygenator(s), heating element(s) condenser(s), a filter and a programmable controller (PLC), for example the central processing unit (CPU) of FIG. 12. Moreover, in view of using the total liquid ventilator system with all types of patients, from premature newborn children to adults, the system according to the illustrative embodiment of the present invention should be made adaptable without the need for re-sizing and changing all components.

Modular and integrated features of the illustrative embodiment of the present invention meet with these requirements. More specifically, the illustrative embodiment of the present invention provides a module integrating in a single unit the following functions: oxygenation, heating, filtration, and condensation. A plurality of these modules can be arranged in series and/or in parallel in order to process a larger amount of liquid, should the necessity arise to ventilate persons of heavier weight.

In addition, the non-restrictive illustrative embodiment of the present invention enables selection of various ventilation cycles, which guide the health-care personnel in the phases prior to ventilation. A start-up phase warms the initial volume of liquid and maintains it at a desired temperature, and oxygenates the liquid at 100% saturation. A filling phase allows the lungs to fill with liquid, by means of a pump included in the ventilator system; the system indicates in real time the quantity of liquid being injected. Finally, the selected ventilation cycle is initiated, thus allowing injection and withdrawal of inspiratory and expiratory volumes of liquid.

The timing, volume and functional parameters for each ventilation cycle are entered on a control panel (for example touch panel 970 of FIG. 12), which communicates continuously with the PLC 980, which in turn controls the entire ventilator. These parameters can be modified during the ventilation cycles. Different options are also available, such as modification of the inspiration and expiration profiles, stopping or starting of the functions, etc.

In order to produce these cycles, the liquid is brought to the patient by means of conduits establishing a simple but complete liquid circuit. The illustrative embodiment of the present invention is provided with only one liquid circuit giving access to all active components of the developed total liquid ventilator. A set of valves and two independent pumps, including a manually operated valve on an endotracheal tube for the isolation of the liquid circuit from the patient's lungs, allow inert liquid to be directed towards the desired component.

Independent control of the two pumps enables correction of the residual volume of liquid contained in the patient's lungs during the ventilation cycles. Such correction is not possible in the case of piston pumps whose pistons are connected to a same platform and moved simultaneously. The amplitude of any required correction is determined through an instrumented buffer reservoir, which indicates the volume of liquid in the total liquid ventilator. This value is used to deduce the volume of liquid in the patient's lungs. In addition, drive of the pumps can be appropriately, independently controlled to increase the oxygenation time during the inspiration phase. Expired PFC liquid thus has additional seconds for shedding its $CO_2$.

According to another feature of the illustrative embodiment of the present invention, the expired liquid entering into the oxygenator is not in direct contact with liquid leaving the oxygenator, due to a division of the inside of this oxygenator into two distinct sections separated by a partition. Oxygenation time is thus increased and elimination of $CO_2$ is greatly promoted.

Details of the non-restrictive illustrative embodiment of the present invention will now be described in connection with FIGS. 1-13 of the appended drawings.

Liquid Circuit

Referring to FIG. 1, the total liquid ventilator system is generally identified by the reference 100.

Ventilator system 100 comprises a liquid circuit including an endotracheal tube 5 having one end 51 inserted in the trachea (not shown) of the patient 6 in accordance with techniques known to those of ordinary skill in the art. The function of the endotracheal tube 5 is to allow liquid to be injected into or withdrawn from the patient's lungs. The other end 52 of the endo-tracheal tube 5 is connected to a Y-connector 9 fitted with a manually operated valve 10. When valve 10 is closed, the liquid circuit is isolated from the patient's airways and lungs. It is then possible to set ventilation cycles that otherwise would send liquid into the patient's lungs.

The function of the Y-connector 9 is to interconnect the ends 231 and 241 of conduits 23 and 24, respectively, to the end 52 of the endotracheal tube 5. The other end 232 of conduit 23 is connected to an inspiration pump 7, which is connected to a buffer reservoir 13 via a conduit 17. Also, the other end 242 of conduit 24 is connected to an expiration pump 8, which communicates with a filter 14, integrated to an oxygenator 11, via a conduit 16.

Components 1, 2, 3 and 4 of FIG. 1 are pinch valves. When valves 1, 2, 3 and 4 are open, flow of liquid through the associated conduits 23, 17, 24 and 16 is enabled. Accordingly, flow of liquid through the various components of the liquid circuit is controlled in relation to the various combinations of opening and closing of these valves 1-4.

The liquid circuit further comprises a network of conduits 19 used to vent a flow of gas from oxygenators 11 and 12 and buffer reservoir 13 towards a PFC condenser 15. Condensed PFC from condenser 15 returns in the form of liquid to the oxygenators 11 and 12 via the conduits 19.

A single oxygenator 11 could be used. However, to improve oxygenation, it is also possible to place an additional oxygenator 12a in series with the oxygenator 12. The gas flow venting from this additional oxygenator 12a is directed through an independent conduit 19a towards an additional condenser 15a dedicated, for example, to oxygenator 12a.

The liquid circuit further comprises a conduit 20 to convey liquid overflow from oxygenator 11 towards oxygenator 12, a conduit 18 to convey liquid overflow from oxygenator 12 towards the optional, additional oxygenator 12a or, when no oxygenator 12a is provided, towards the buffer reservoir 13. When an optional, additional oxygenator 12a is provided, a conduit 18a is provided to convey liquid overflow from this additional oxygenator 12a to the buffer reservoir 13.

In the following description, the pumps 7 and 8 will be described as piston pumps. However, it should be kept in mind that the illustrative embodiment of the present invention is not limited to the use of piston pumps; any other type of pump capable of fulfilling the required function could be used.

In the same manner, in the following description, the liquid will be described as a PFC liquid. However, it should be kept in mind that the illustrative embodiment of the present invention is not limited to the use of PFC liquid; any other type of liquid capable of fulfilling the required function could be used.

Cycle with Patient

When valve 2 is open and valve 1 is closed, the piston of inspiration pump 7 is operated to fill pump 7 with oxygenated PFC liquid from buffer reservoir 13 via conduit 17. In this case, the PFC liquid flows in the direction indicated by the arrow 22.

Subsequently, when valve 1 is open and valves 2 and 3 are closed, the piston of inspiration pump 7, filled with oxygenated PFC liquid, can be operated to pump PFC liquid through conduit 23 towards Y-connector 9. This Y-connector 9 directs the pumped oxygenated PFC liquid towards the lungs of the patient 6 via the endotracheal tube 5. The PFC liquid then flows in the direction indicated by the arrow 26.

When valve 3 is open and valves 2 and 4 are closed, the piston of expiration pump 8 can be operated to withdraw PFC liquid from the patient's lungs through the endotracheal tube 5, the Y-connector 9, and the conduit 24. The direction of PFC liquid flow thus created is indicated by the arrow 25 of FIG. 1.

When valve 3 is closed and valve 4 is open, the PFC liquid accumulated in the pump 8 can be expelled through conduit 16 toward the filter 14 integrated to the oxygenator 11 in the direction of the arrow 21.

Cycle without Patient

When valves 1, 2 and 3 are open and valves 4 and 10 are closed, expiration pump 8 can draw PFC liquid from buffer reservoir 13 through conduit 17, pump 7, conduit 23, Y-connector 9 and conduit 24. In the same manner, when valves 1, 3 and 4 are open and valves 10 and 2 are closed, inspiration pump 7 is capable of transferring PCT liquid directly to filter 14 via conduit 23, Y-connector 9, conduit 24, pump 8 and conduit 16.

Thus, valve 10 mounted on the Y-connector 9 allows PFC liquid to flow within the total liquid ventilator system 100. Valve 10 also enables connection of a gas ventilator during filling of the patient's lungs with PFC liquid. Moreover, valve 10 facilitates the substitution of tubes from the liquid and gas ventilators during filling of the patient's lungs with PFC liquid.

Sequences

Start-Up Cycle

In order to initially fill the total liquid ventilator system 100, PFC liquid containing little oxygen is supplied at room temperature to the system. Then, a start-up cycle is implemented to circulate the PFC liquid in a closed-loop circuit in the total liquid ventilator system 100, and thereby warm and oxygenate the PFC liquid. More specifically, the PFC liquid flows through oxygenators 11 and 12 (and eventually 12a) to increase its oxygen contents to saturation. At the same time, the PFC liquid is warmed by a heating system (not shown) integrated to oxygenators 11 and 12 (and eventually 12a). Once the target temperature is reached, the heating system is operated only to compensate for thermal losses and maintaining the PFC liquid at this target temperature. The start-up cycle thus oxygenate and warm the PFC liquid, and maintain this PFC liquid at the desired temperature prior to proceeding with subsequent filling and ventilation cycles.

During the start-up cycle, valve 10 of the Y-connector 9 is closed. Valves 1 and 2 are opened and the piston of inspiration pump 7 positioned to prevent PFC liquid to enter the pump. Then valve 4 is closed, valve 3 is opened, and the piston of expiration pump 8 is operated to fill pump 8 with PFC liquid from the buffer reservoir 13 via conduit 17, conduit 23, Y-connector 9, and conduit 24. Once pump 8 is filled, valve 3 is closed, valve 4 is opened, and the piston of expiration pump 8 is operated to expel the PFC liquid from the pump 8 toward the filter 14 of the oxygenator 11 via conduit 16.

Filling Sequence

The filling sequence is used to fill the lungs of the patient 6 through the expiration pump 8 and the liquid circuit of the ventilator system 100. Prior to this sequence, the health-care personnel set the filling parameters on the control panel (for example touch panel 970 of FIG. 12) in order to establish, for example, the flow delivery rate of the pump 8 and the FRC (functional residual capacity) volume. The FRC volume can be defined as the volume of liquid remaining in the lungs at the end of a quiet expiration.

This filling sequence begins with opening of valves 1, 2 and 3 and closure of valves 4 and 10. The piston of the expiration pump 8 is then operated until this pump 8 is filled with PFC liquid from the buffer reservoir 13 through conduit 17, conduit 23, Y-connector 9 and conduit 24. Finally, valve 1 is closed, valve 10 is opened, and the health-care personnel operate the control panel (for example touch panel 970 of FIG. 12) of the PLC 980 to fill the lungs 6 with a desired volume, by simply operating the piston of the expiration pump 8 to transfer the desired volume of PFC liquid from the pump 8 to the patient's lungs through the conduit 24, the Y-connector 9 and the endotracheal tube 5.

The use of the expiration pump 8 to fill the patient's lungs allows inspiration pump 7 to fill in turn, during the filling sequence, with one tidal volume determined and entered on the control panel (for example touch panel 970 of FIG. 12) by the health-care personnel. The ventilation cycle can thus begin immediately as soon as filling of the patient's lungs with PFC liquid is completed.

Ventilation Cycle

Figure 2:
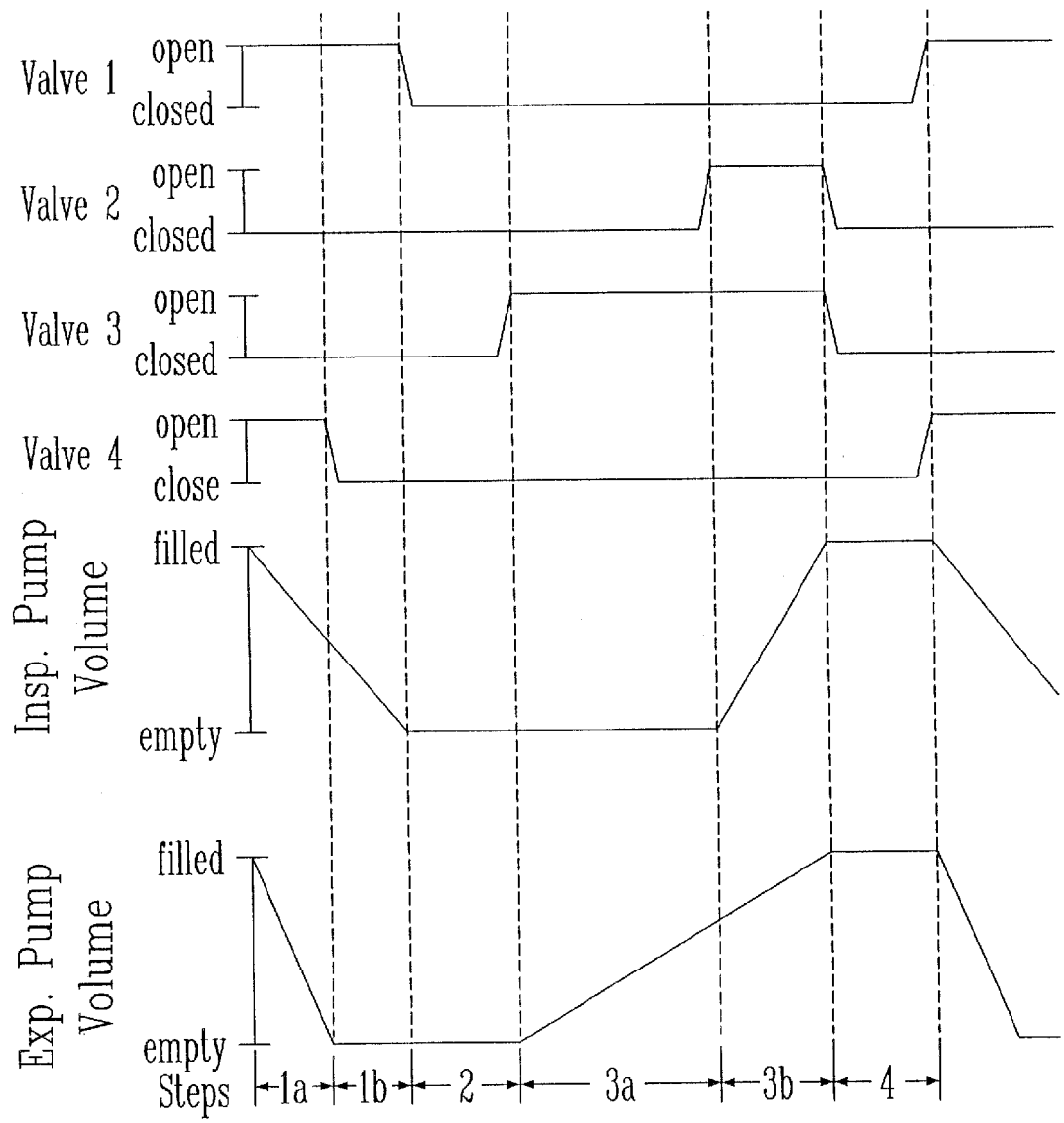
FIG. 2 is a graph showing the sequence of operation of the different components of the total liquid ventilator system of FIG. 1, during a ventilation cycle.

The ventilation cycle of the non-restrictive illustrative embodiment of the present invention is divided into four (4) steps, namely inspiration, a pause at the end of inspiration, expiration, and a pause at the end of expiration. FIG. 2 is a graph showing the various steps executed and controlled by the PLC 980 during a ventilation cycle.

Figure 12:
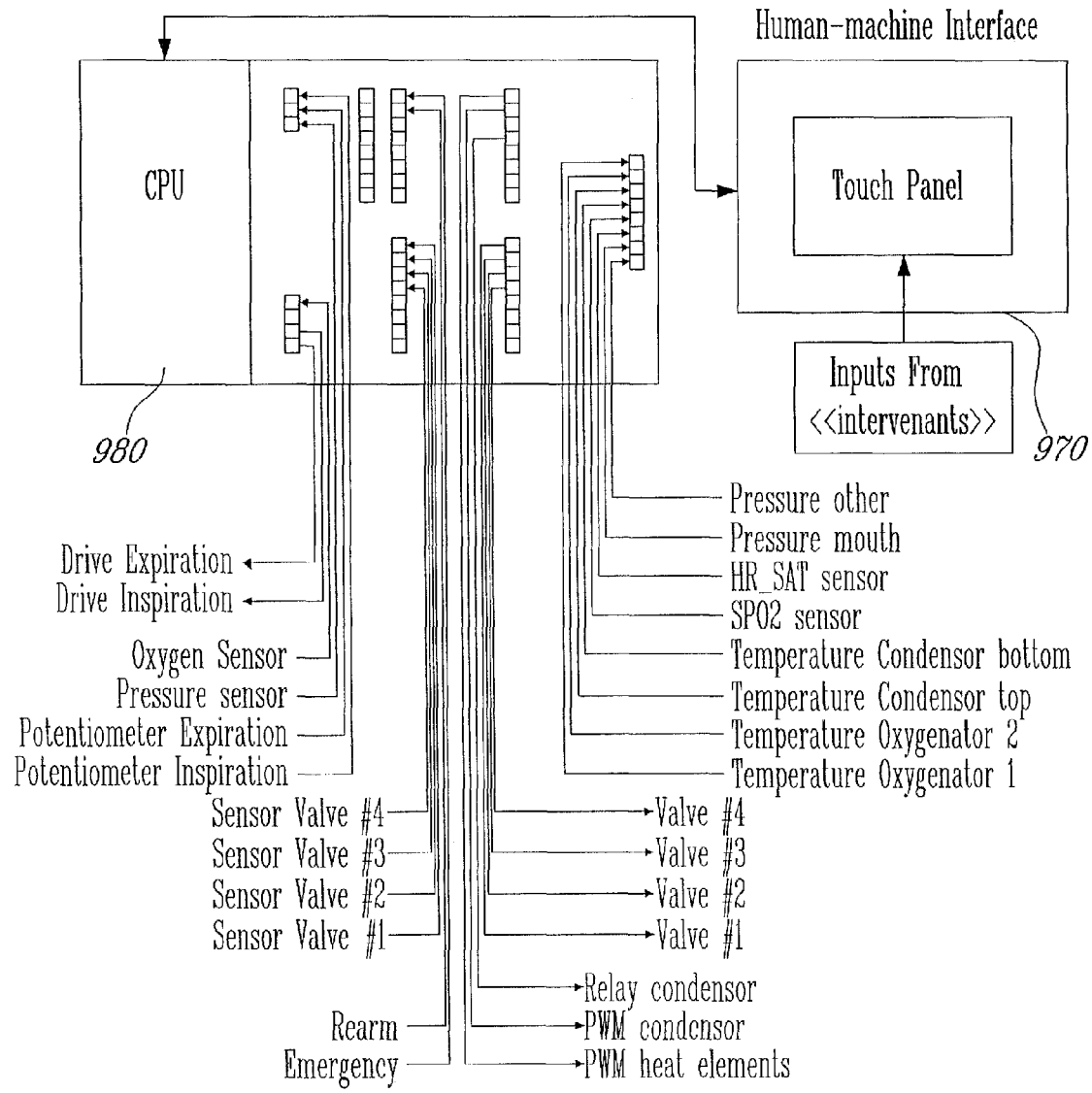
FIG. 12 is a schematic block diagram showing the components of the non-restrictive illustrative embodiment of the total liquid ventilator system connected to a PLC (Programmable logic controller) along with a control panel.

Timing and volume parameters (for example 75 in FIG. 10) are determined by the health-care personnel and entered into the PLC 980 of FIG. 12 via the control panel (for example touch panel 970 of FIG. 12). These timing and volume parameters can be modified during total liquid ventilation to improve and/or correct various situations encountered during total liquid ventilation.

Step 1

Inspiration

As illustrated in FIG. 2, valve 1 is open and valve 2 is closed during step 1. The piston of inspiration pump 7 is operated to transfer PFC liquid contained in pump 7 to the patient's lungs through conduit 23, Y-connector 9 and endotracheal tube 5. Valve 1 is closed at the end of step 1.

During phase 1a of step 1, valve 4 is open and valve 3 is closed. The piston of expiration pump 8 is operated to expel and transfer the PFC liquid contained in pump 8 toward filter 14 through conduit 16. Transfer of PFC liquid contained in pump 8 toward filter 14 is faster than transfer of the PFC liquid contained in pump 7 to the patient's lungs. After expiration pump 8 is completely empty, valve 4 is closed.

Phase 1b corresponds to a pause, or latent time between the end of the transfer of PFC liquid contained in pump 8 toward filter 14 and the end of the transfer of the PFC liquid contained in pump 7 to the patient's lungs following inspiration. This pause or latent time can be recovered as oxygenation time, due to the fact that the pumps 7 and 8 are controlled individually. The PFC liquid thus benefits from extra seconds to be oxygenated and to discharge the $CO_2$ it contains.

Step 2

Pause #1—End of Inspiration

When inspiration step 1 is completed, a pause (see step 2 in FIG. 2) is desirable to measure the pressure in the lungs of the patient 6. These measurements will enable evaluation of certain lung parameters such as static compliance.

Step 3

Expiration

During expiration phase 3, valve 3 is open and valve 4 is kept closed. The piston of expiration pump 8 is operated to withdraw PFC liquid from the patient's lungs through the endotracheal tube 5, the Y-connector 9 and the conduit 24 in the direction indicated by arrow 25.

During phase 3a, the piston of inspiration pump 7 is stationary and valves 1 and 2 are closed. It is then possible to measure the level of PFC liquid inside the buffer reservoir 13 through a liquid level sensor 88 (FIG. 1). With knowledge of the efficiency of the condenser 15 (and eventually the condenser 15a), this level measurement can be used to determine whether or not losses of PFC liquid from the liquid circuit or errors in the volumes injected into or withdrawn from the patient's lungs have occurred.

During phase 3b of step 3, the piston of inspiration pump 7 is operated to fill pump 7 with PFC liquid from the buffer reservoir 13 via a conduit 17. Of course, valve 2 is open to allow PFC liquid to flow in the direction of the arrow 22. When inspiration pump 7 contains the volume of PFC liquid determined by the health-care personnel and entered in the ventilation system through the control panel (for example touch panel 970 of FIG. 12), valve 2 is closed.

Step 4

Pause #2—End of Expiration

At the end of expiration step 3 (FIG. 2), a second pause (step 4) will make it possible to measure the pressure in the patient's lungs. These measurements will be used to evaluate certain lung parameters such as static compliance.

The cycle then returns to step 1 and does so repeatedly until the health-care personnel terminates the total liquid ventilation procedure.

It should be mentioned that independent control of the inspiratory 7 and expiratory 8 pumps is required to obtain the ventilation cycle profile of FIG. 2.

In FIG. 2, ramp profiles are used during inspiration step 1 and expiration step 3. However, this is within the scope of the present invention to use other types of profiles, for example decreasing exponential profiles with parameters different for the inspiration and expiration in view of optimizing the ventilation. For example, the pump flow rate can be expressed as a function of time as follows:

$$q(t) = \frac{A e^{-t/\tau}}{\tau}$$

where $\tau$ is a time constant adjusting the profile, and $$A = \frac{VT}{e^{-Texp/\tau} - 1},$$

and VT is the tidal volume.

Lung Emptying Sequence

When emptying of the lungs of the patient 6 is desired, the ventilation cycle is first completed. This ventilation cycle terminates with the expiration step. To empty the patient's lungs, it is sufficient to close the manual valve 10, disconnect the endotracheal tube 5 from the Y-connector 9, and then tilt the patient 6 in view of draining the PFC liquid from the lungs by gravity.

Estimation of FRC (Functional Residual Capacity)

As indicated in the foregoing description sensor 88 is used to measure the level of PFC liquid contained in the buffer reservoir 13. Knowing the efficiency of the condenser 15 (and eventually the condenser 15a), this level measurement can be used to determine whether or not losses of PFC liquid from the circuit or errors in the volumes injected into or withdrawn from the patient's lungs have occurred.

The theoretical functional residual capacity (FRC) is calculated using the following Equation (1) while the estimated FRC is calculated using the following Equation (2). The indicator k refers to the ventilation cycle number.

$$V_{crf}[k+1] = V_{crf}[k] + V_{ti}[k] - V_{te}[k] \quad (1)$$

$$\hat{V}_{crf}[k+1] = V_{crf}(0) - (V_{ar}[0]*(1-at) - V_{ar}[k]) \quad (2)$$

where,
- $V_{crf}$, volume of the functional residual capacity (ml);
- $V_{ti}$, tidal volume in inspiration pump 7 at step 4 (ml);
- $V_{te}$, tidal volume in expiration pump 8 at step 4 (ml);
- $V_{ar}[0]$, initial volume in the buffer reservoir 13 (ml);
- a, loss in the condenser per unit of time (ml/s); and
- $V_{ar}$, volume in the buffer reservoir during step 3a (ml).

The two values for the volume of the functional residual capacity must be in agreement with each other to conclude that the volume of PFC liquid in the patient's lungs remains constant. Increases in the value of $\hat{V}_{crf}$ compared to $V_{crf}$ indicate that the volume of PFC liquid in the patient's lungs is decreasing, while decreases in $\hat{V}_{crf}$ compared to $V_{crf}$ indicate that the volume of PFC liquid in the lungs of the patient is increasing.

Independent control of the inspiration and expiration pumps 7 and 8 allow correction of the FRC during total liquid ventilation by using an inspiration volume different from the expiration volume or vice-versa. Thus, to increase the FRC, the inspiration volume will be greater than the expiration volume for a determined number of ventilation cycles. In the same manner, to decrease the FRC, the inspiration volume will be smaller than the expiration volume for a given number of ventilation cycles.

Thus, the non-restrictive, illustrative embodiment of the present invention presents, amongst others, the following features:

- The buffer reservoir 13 is used to estimate the quantity of PFC liquid present within the total liquid ventilator system and, therefore, to determine by deduction the residual volume of PFC liquid in the lungs of the patient 6;
- The independent control of the pistons of the inspiration and expiration pumps 7 and 8 facilitates the implementation of the start-up cycle;
- Independent control of the operation of the pistons of the inspiration and expiration pumps 7 and 8 maximizes the time of residence of the PFC liquid inside the gas oxygenators. In fact, as soon as the PFC liquid is withdrawn from the patient's lungs, the piston of the expiration pump 8 quickly expels the PFC liquid from this pump 8 towards the filter 14 and oxygenator 11 at a flow rate higher than that of the inspiration pump 7;
- Independent control of the pumps 7 and 8 enables correction of the FRC volume over one or several ventilation cycles:
  - The FRC volume can be increased or decreased during expiration while leaving the inspiration liquid volume constant; and
  - The FRC volume can be increased or decreased during inspiration while leaving the expiration liquid volume constant; and
- The following parameters can be modified in the course of total liquid ventilation:
  - Inspiration and expiration tidal volume;
  - Expiration time;
  - The duration of the first pause (phase 1b of step 1 and step 2 of FIG. 2);
  - The duration of the second pause (step 4 of FIG. 2);
  - Inspiration step profile; and
  - Expiration step profile.

The structure and operation of components of the non-restrictive illustrative embodiment of total liquid ventilator system according to the present invention will now be described with reference to FIGS. 3-13. The structure and operation of these components will be described as example only, and it is within the scope of the present invention to use any other type of components capable of fulfilling the corresponding functions.

Oxygenator

Figure 3:
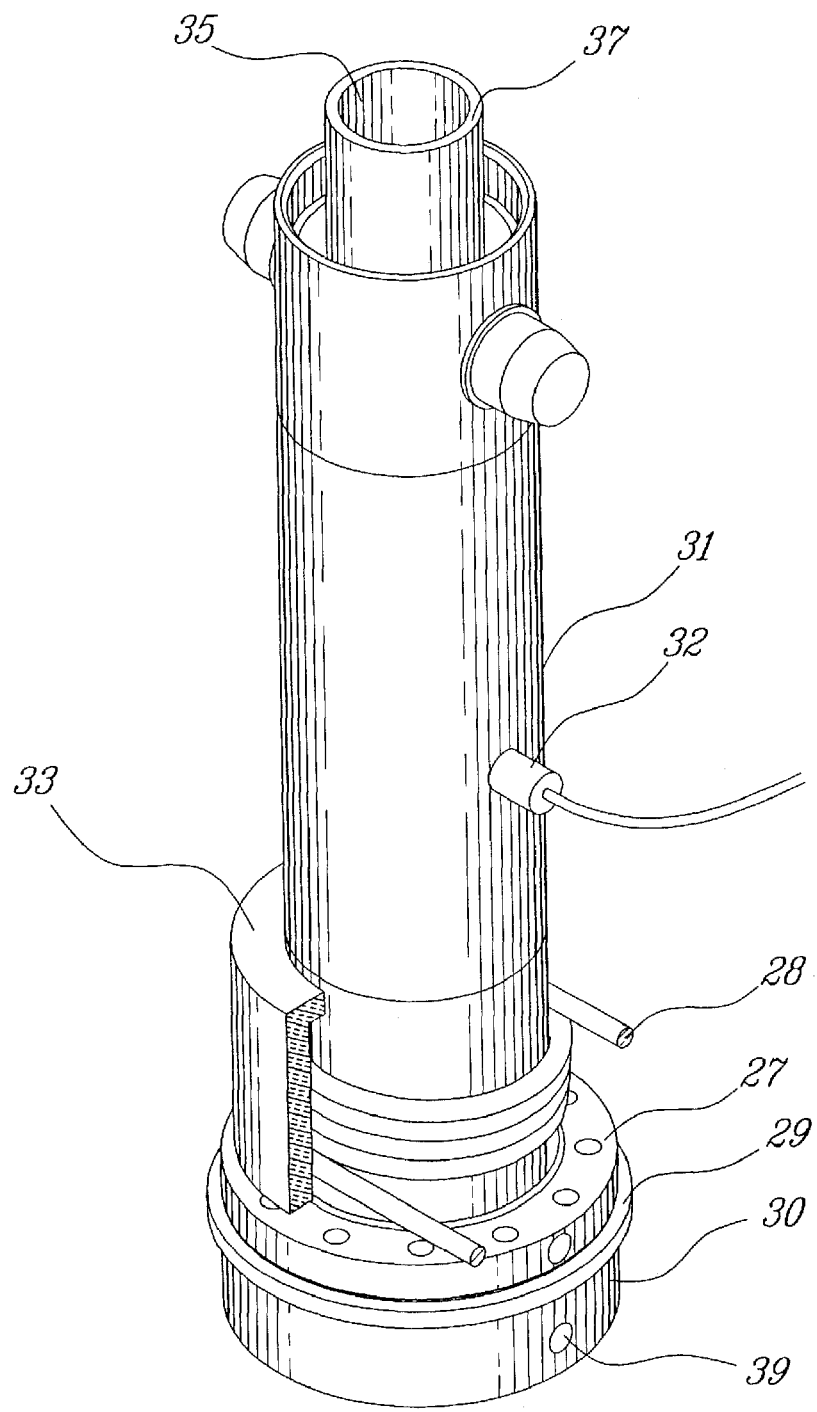
FIG. 3 is an isometric view of an oxygenator module forming part of the non-restrictive illustrative embodiment of the total liquid ventilator system of FIG. 1, including a partial cut-away portion showing a heating element integrated to the oxygenator module.
Figure 4:
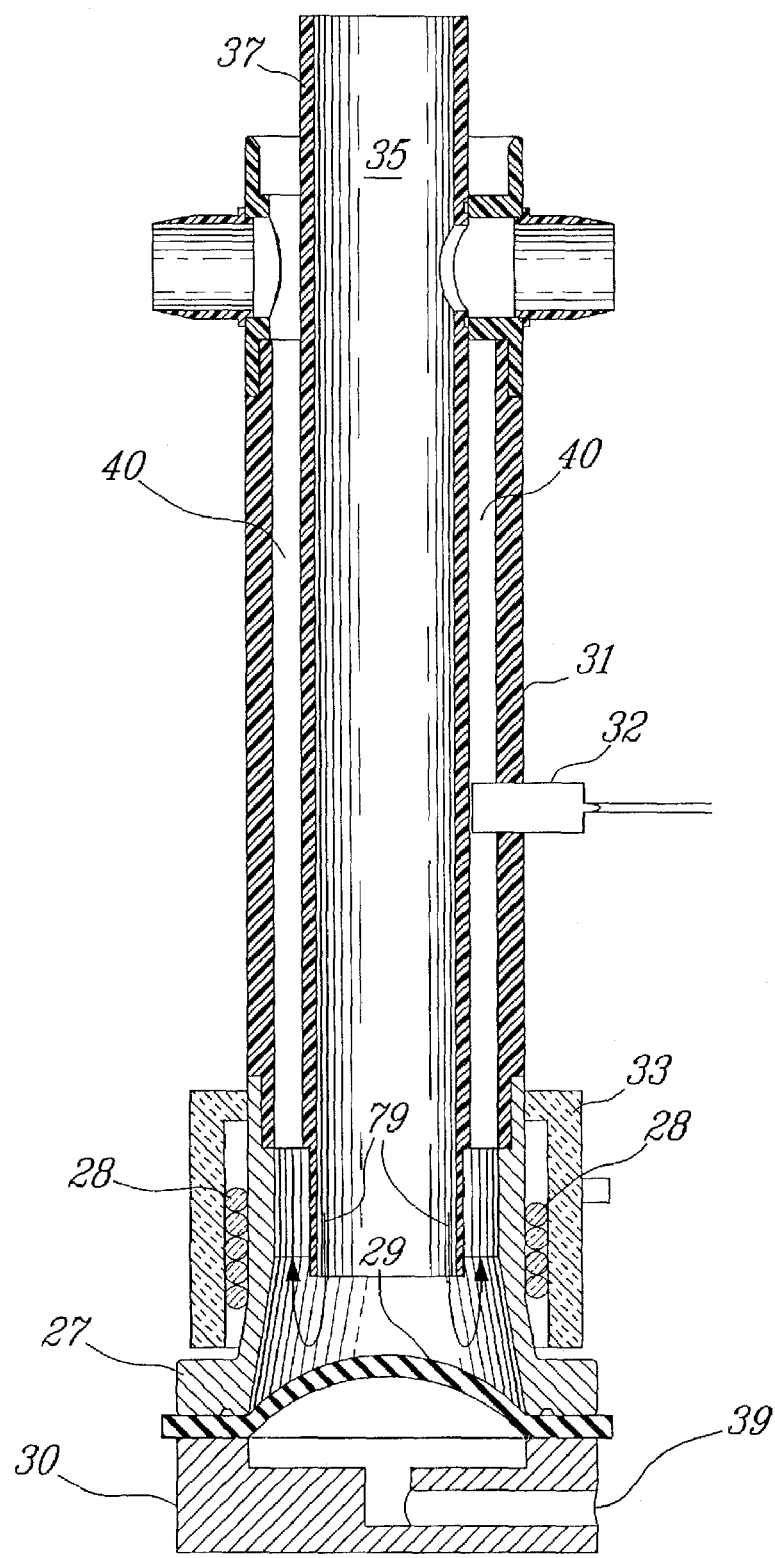
FIG. 4 is a cross-sectional view of the oxygenator module of FIG. 3, shows compartments and the path followed by PFC liquid in the module.
Figure 5:
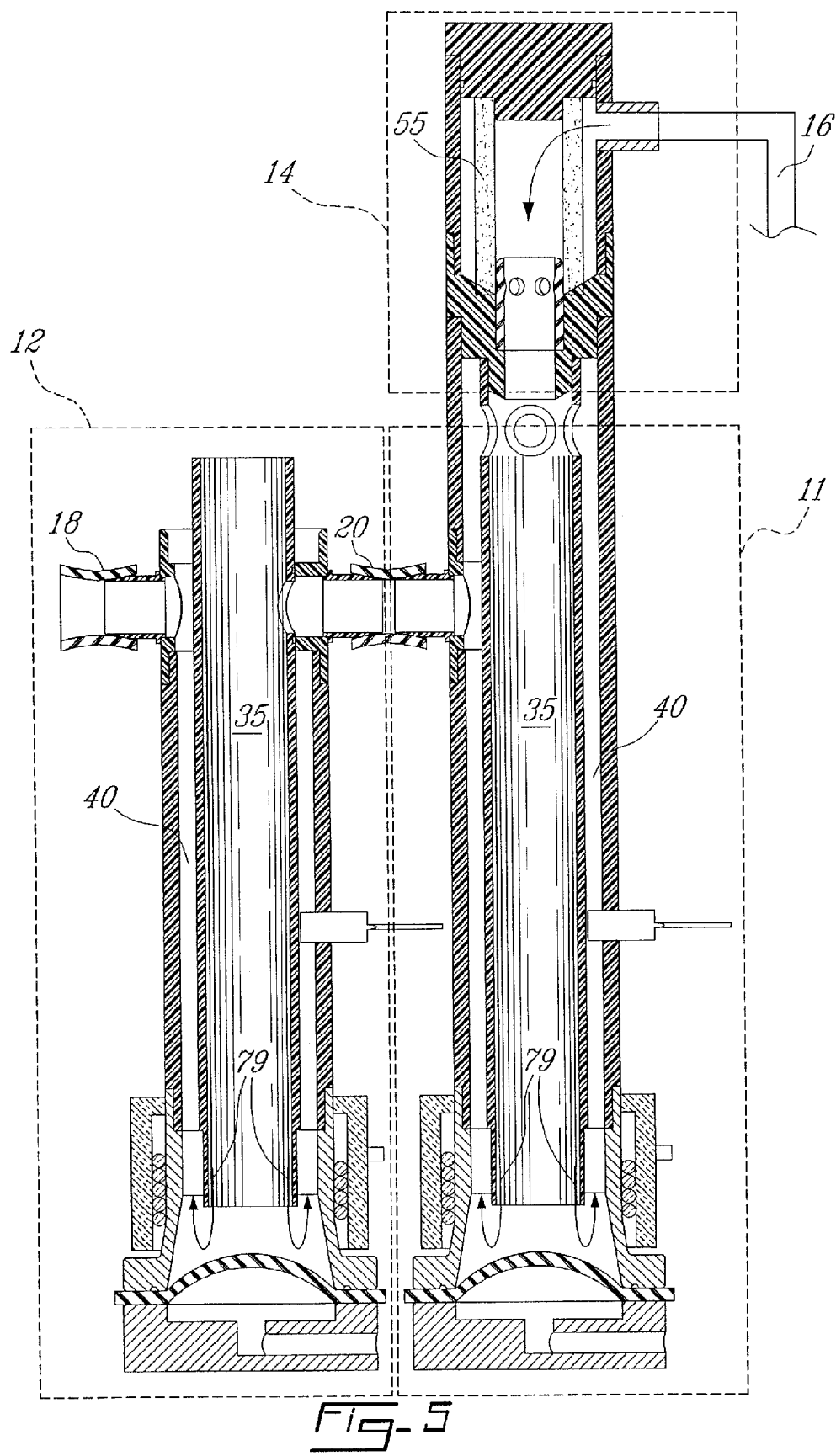
FIG. 5 is a cross-sectional view of an assembly of two oxygenator modules according to the non-restrictive illustrative embodiment of the total liquid ventilator system, showing heating and filtration elements as well as a path of the liquid flow through these modules and elements.

The primary function of the oxygenators 11, 12 and 12a is to maintain the quantity of oxygen in the PFC liquid at the level of saturation. In order to meet this objective, an oxygenator of the bubbler type was developed. FIG. 3 is an isometric view of the developed oxygenator, while FIG. 4 is a cross-sectional view thereof. FIG. 5 is a cross-sectional view of the oxygenators 11 and 12, showing the elements joining them together.

Referring to FIGS. 3-5, bubbles of pure oxygen are generated at the base of each oxygenator through a perforated membrane 29, held firmly in position between an annular base 30 and a tubular lower portion 27. Oxygen is supplied beneath membrane 29 through an input line 39 formed in the base 30. The generated bubbles enter directly into contact with PFC liquid contained in tubular section 35 and annular section 40. Gas flow vented from the top of oxygenators 11 and 12 reaches the condenser 15 via the network of conduits 19. The PFC vapour contained in this gas flow condenses in the condenser 15 and returns in liquid state to the oxygenators 11 and 12 via the network of conduits 19.

The same structure and operation equally apply to oxygenator 12a and condenser 15a.

The inside of each oxygenator 11, 12 and 12a is divided into two sections, an inner tubular section 35 delimited by an inner tube 37, and an outer annular section 40 delimited by tubes 31 and 37. Sections 35 and 40 communicate with each other at the bottom of the oxygenator, since the lower end of tube 37 is spaced apart from the perforated membrane 29. The volumetric capacity of sections 35 and 40 of the oxygenator is of the order of one tidal volume.

Figure 7:
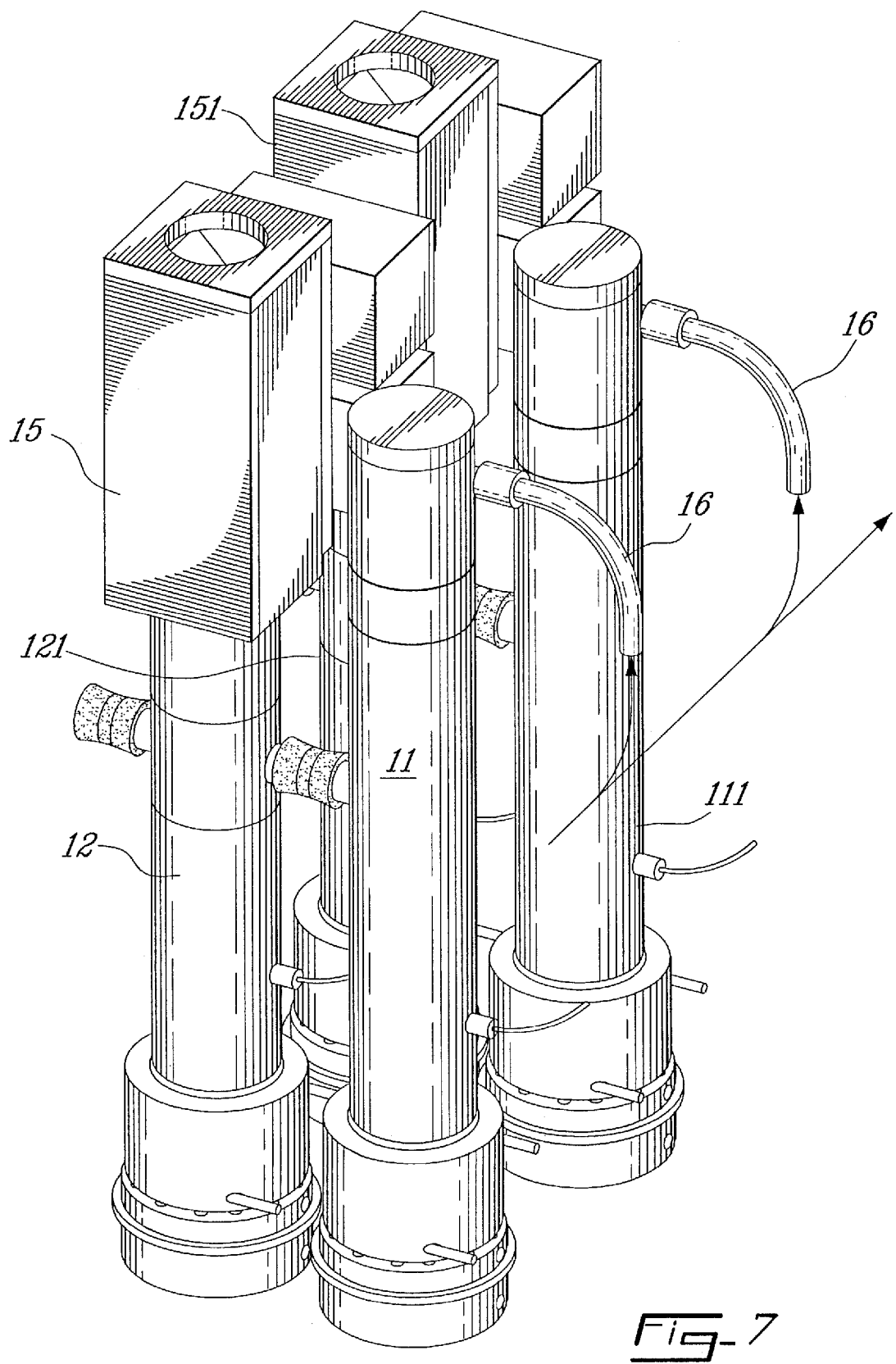
FIG. 7 is an isometric view of one example of assembly of oxygenator modules.
Figure 8A:
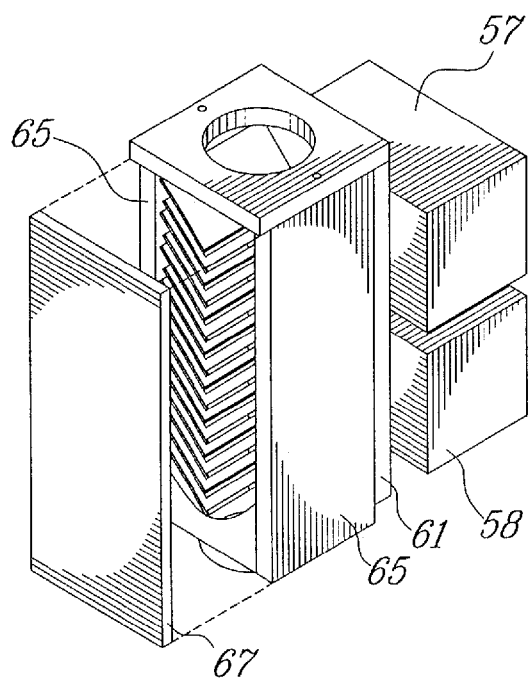
FIG. 8a is an isometric view of one example of condenser module for recovering PFC liquid in a gas flow from oxygenator modules and from a buffer reservoir.
Figure 8B:
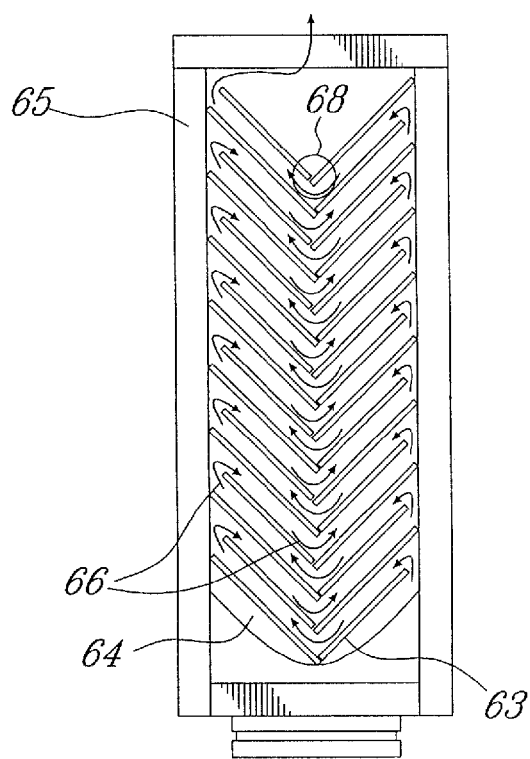

Depending on the weight of the patient 6 and the quantity of PFC liquid to be oxygenated, it is possible to modify either the cross-sectional area or the height of the tubes 31 and 37 and/or the number of oxygenators. Increasing the number of oxygenators may be done in series or parallel according to requirement of the intended application. FIG. 1 shows the series option while FIG. 7 shows the parallel option.

During each ventilation cycle, liquid brought by conduit 16 flows through filtration element 55 (FIG. 5) of filter 14 integrated to the oxygenator 11. The filtered PFC liquid is then supplied to the inner section 35 of the oxygenator 11. The increase in liquid volume in section 35 forces PFC liquid from tubular section 35 to annular section 40 through the space between the lower end of the tube 37 and the membrane 29 as indicated by the arrows 79. This ensures that non-oxygenated PFC liquid supplied to the upper portion of tube 37 does not come into contact with oxygenated PFC liquid leaving the oxygenator, to improve discharge of $CO_2$ and increase the effective time of residence of the PFC liquid within the oxygenator.

The liquid flow identified by the arrows 79 tends to equilibrate the levels of PFC liquid in the different sections 35 and 40 of each oxygenator.

However, as soon as the level of PFC liquid in annular section 40 of oxygenator 11 reaches conduit 20, the overflow is directed toward the inner tubular section 35 of the second oxygenator 12. This overflow mechanism maintains the overall liquid level of oxygenators 11 and 12 at the height of the overflow conduits 18 and 20. The same overflow liquid transfer also occurs from the outer annular section 40 of the second oxygenator 12 toward the inner tubular section 35 of the third, optional oxygenator 12a.

Thus:
- The partition of the oxygenator volume into radially spaced apart sections imposes on the PFC liquid a flow path from top to bottom in the inner tubular section and then from bottom to top in the outer annular section before it can leave. This prevents non-oxygenated PFC liquid supplied to the inner tubular section from coming into direct contact with oxygenated PFC liquid leaving the outer annular section, thus increasing the time of contact between PFC liquid and oxygen.
- A plurality of oxygenator such as 11 and 12 can be connected in series or in parallel through simple tubes, since liquid transfer from one oxygenator to the other is conducted by overflow. This makes the assembly of oxygenators modular.
- The number of oxygenators determines the quality of the gaseous exchange and connecting them in series or in parallel increases this efficiency.
- The number of oxygenators is adjustable as a function of the weight of the patient. Knowing the weight of the patient, the amount of $CO_2$ per expiration dissolved in the PFC liquid and, therefore, the required time of residence of the PFC liquid the oxygenator(s) can be determined.
- The filter is easily accessible and can be changed during total liquid ventilation.
- The filter is integrated directly into the oxygenator 11. This structure reduces the amount of PFC liquid required by the ventilator to operate. Also, no tubes are required to connect the filter to the oxygenators.

Heating System

The function of the heating system is to warm the initial volume of PFC liquid supplied to the total liquid ventilator system, and to maintain this PFC liquid at the required temperature. In order to minimize the quantity of liquid required by the ventilator system to operate, the heating system is integrated into the lower portion of the oxygenator(s).

As illustrated in FIG. 3, a 120 W heating element 28 is wound around the lower tubular portion 27, made of metal, to increase the temperature of this portion 27. The warmed tubular portion 27, in turn, warms the PFC liquid it contains. Bubbles generated through the membrane 29 ensure constant agitation of the PFC liquid, producing a uniform temperature distribution throughout sections 35 and 40. An annular sheath 33, made of heat-insulating material, prevents the health-care personnel from touching the heating element 28 and tubular portion 27.

Figure 6:
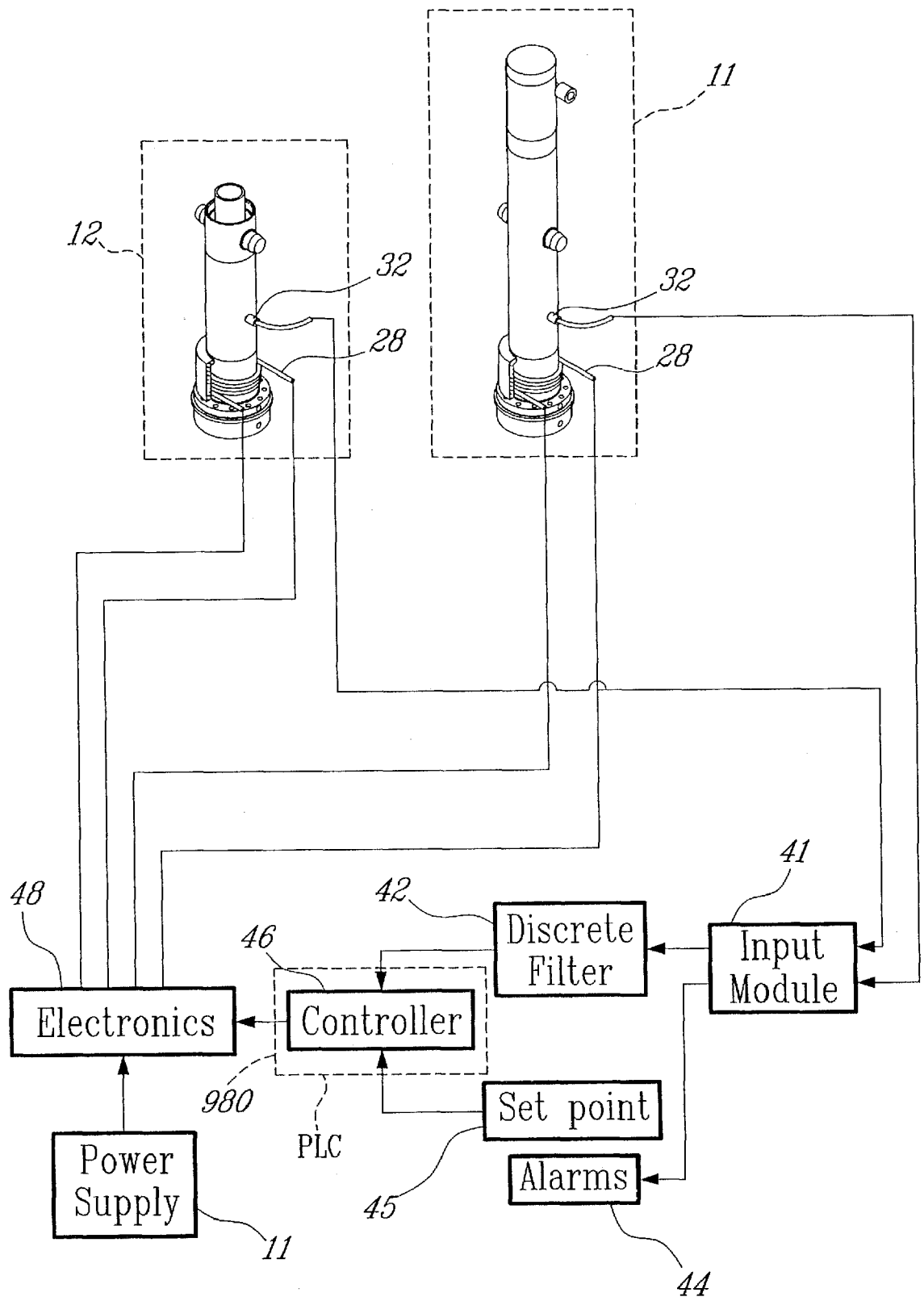
FIG. 6 is a schematic block diagram showing a circuit for controlling the liquid temperature in the oxygenation modules.

FIG. 6 illustrates a system for controlling the level of temperature of the PFC liquid. A temperature sensor 32 is mounted on the tube 31 of each oxygenator to measure the temperature of the PFC liquid within section 40. The measurements of temperature from every oxygenator such as 11, 12 and 12a are first processed through an input module 41 of the PLC 980. The input module 41 averages the different measurement signals to produces a temperature signal filtered through a discrete filter 42 to remove high frequency components therefrom. The filtered temperature signal is then transferred to a controller 46 forming part of the PLC 980 of FIG. 12, which compares this filtered temperature signal with a temperature set-point 45 determined by the health-care personnel and entered through the control panel (for example touch panel 970 of FIG. 12). The output signal from the controller 46 is applied to an electronic power transfer device 48, which modulates electric power from the supply 49 to the heating element 28 of each oxygenator (such as 11, 12 and 12a).

The unfiltered temperature signals from the various temperature sensors 32 are also used to signal alarms 44, for example too low a temperature of the PFC liquid, too high a temperature of the PFC liquid, and malfunctioning of the heating system in situations of incoherence between measured temperature values.

Consequently:
- The use of electric heating elements wound on the outside of the lower tubular portions 27 of the oxygenators such as 11, 12, 12a, reduces the overall dimensions of the total liquid ventilation system while providing accurate temperature control.
- The heating system is integrated to the lower tubular portions 27 of the oxygenators to reduce the volume of PFC liquid required by the ventilator system to operate.

Condenser System

The function of the condenser(s), for example 15 and 15a (FIG. 1), is to recover PFC matter escaping under the form of vapour or aerosol from the oxygenator(s), for example oxygenators 11, 12 and 12a, and from the buffer reservoir 13. In the non-restrictive example of FIG. 1, condenser 15 is dedicated to oxygenators 11 and 12 while condenser 15a recovers PFC liquid escaping from oxygenator 12a. Installation of a second series of oxygenator(s), for example oxygenators 111 and 121 of FIG. 7, in parallel to the first series of oxygenator, for example oxygenators 11 and 12, requires an additional condenser, for example condenser 151 of FIG. 7, to recover the PFC vapour and aerosol from the oxygenator(s) of this second series. Moreover, when the capacity of a single condenser is insufficient, the gas flow from the oxygenator(s) can be split and distributed among several condensers placed in a parallel arrangement. To meet this requirement, the condenser should be designed as a modular unit.

In the non-restrictive illustrative embodiment of the total liquid ventilator system, the condenser(s), for example condensers 15 and 15a, are fin tube thermal exchangers. Fins 63 and 64 (FIGS. 8a and 8b) are stacked in a V arrangement and mounted on a metallic planar base 61 cooled by thermoelectric modules (TEM) 57 and 58. To maximize the thermal exchange surface and to increase efficiency, shorter fins 63 alternate with longer fins 64. Since the fins 63 and 64 are enclosed within walls 65 and 67, flow of gas follows the path indicated by arrows such as 66. Along the path 66 through the condenser, the temperature of the gas flow decreases and PFC vapours and aerosol condense on the surface of the fins 63 and 64 to finally to drain through the slots 68 at the apexes between the fins 63 and 64 and return to the oxygenator(s) through the network of conduits, for example network 19 of FIG. 1.

Figure 9:
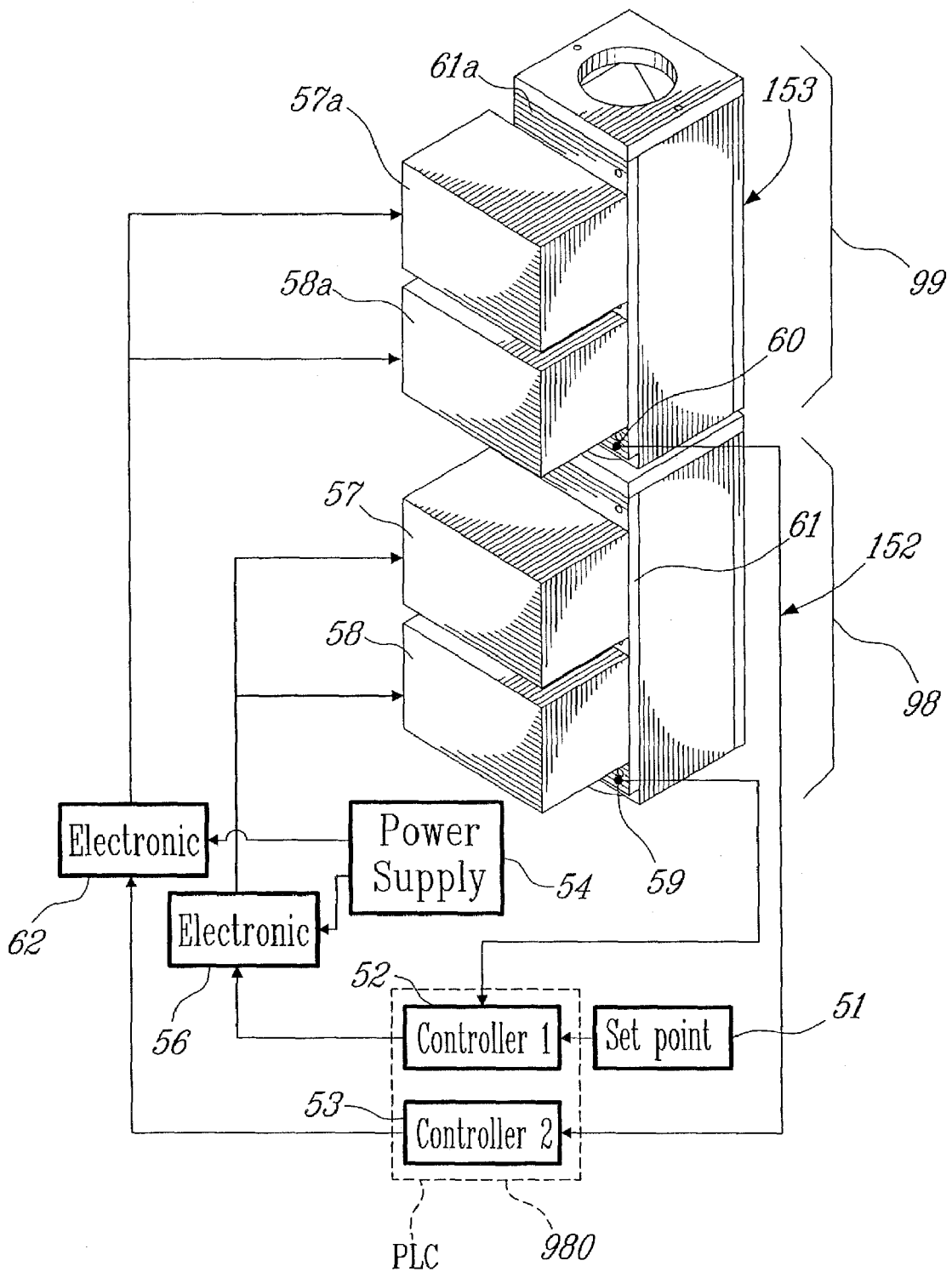
FIG. 9 is an isometric view illustrating one example of a serial assembly of condenser modules, with a schematic block diagram describing control of the condenser modules.

FIG. 9 shows the modularity of the condenser used in the non-restrictive illustrative embodiment of the present invention. The purpose of placing two identical condensers in series is to increase the overall efficiency of recovery of PFC vapours and aerosol contained in the gas flow from the oxygenator(s). To achieve this goal, two control strategies are implemented, one for stage 98 (first condenser 152) and the other for stage 99 (second condenser 153).

The function of the first condensation stage 98 is to remove the major portion of the PFC vapours and aerosol. The condenser 152 must therefore be kept at a temperature that prevents icing but maximizes PFC liquid recovery efficiency. The task of a controller 52 forming part of the PLC 980 of FIG. 12 is to maintain this level of temperature. For that purpose, the controller 52 compares the temperature of the base 61 of the first condenser 152 measured by a sensor 59 with a set-point 51 entered by the health-care personnel through the control panel (for example touch panel 970 of FIG. 12) and sends the result of this comparison to an electronic power transfer device 56 that modulates electric power supplied to the thermoelectric elements 57 and 58 from supply 54 in order to maintain the desired temperature.

The task of the second stage 99 is to extract PFC vapours and aerosol remaining in the gas flow from the first stage 98. A controller 53 forming part of the PLC 980 of FIG. 12 produces icing/de-icing cycles. Initially, the metallic planar base 61a is cooled to a temperature sufficiently low to solidify PFC vapours and aerosol remaining in the gas flow. When a sufficient quantity has accumulated on the fins 63 and 64, the controller 53 activates the de-icing phase by reversing, by means of an electronic device 62, the polarity of a voltage applied across the thermoelectric modules 57a and 58a by the power supply 54. The cold plate 61a is then heated for a brief instant in order to liquefy the accumulated frozen PFC liquid. Once the fins 63 and 64 are completely de-iced, the icing phase is repeated. The controller 53 controls this icing/de-icing cycle in response to the temperature of the metallic base 61 detected through a sensor 60 and, as indicated in the foregoing description, through the power electronic device 62.

Consequently:
- The condenser considerably reduces losses of PFC liquid while ensuring excellent gas flow.
- The condenser controller of the second stage 99 introduces icing/de-icing cycles to improve recovery of PFC liquid, reduce losses of PFC liquid to near zero, and improve efficiency.
- The modular nature of the condenser enables the construction of various configurations, including a parallel arrangement of condensers to process larger volumes of gas from the oxygenator(s) and a series arrangement of condensers to increase the efficiency of recovery of PFC liquid.
- Integration of the condenser and oxygenator facilitate their connection to other components of the total liquid ventilator system, thus making this system of simpler construction.
- Independent control of the condensers permits the implementation of various control strategies for the purpose of increasing the efficiency of PFC liquid recovery.

Pump System

Figure 10:
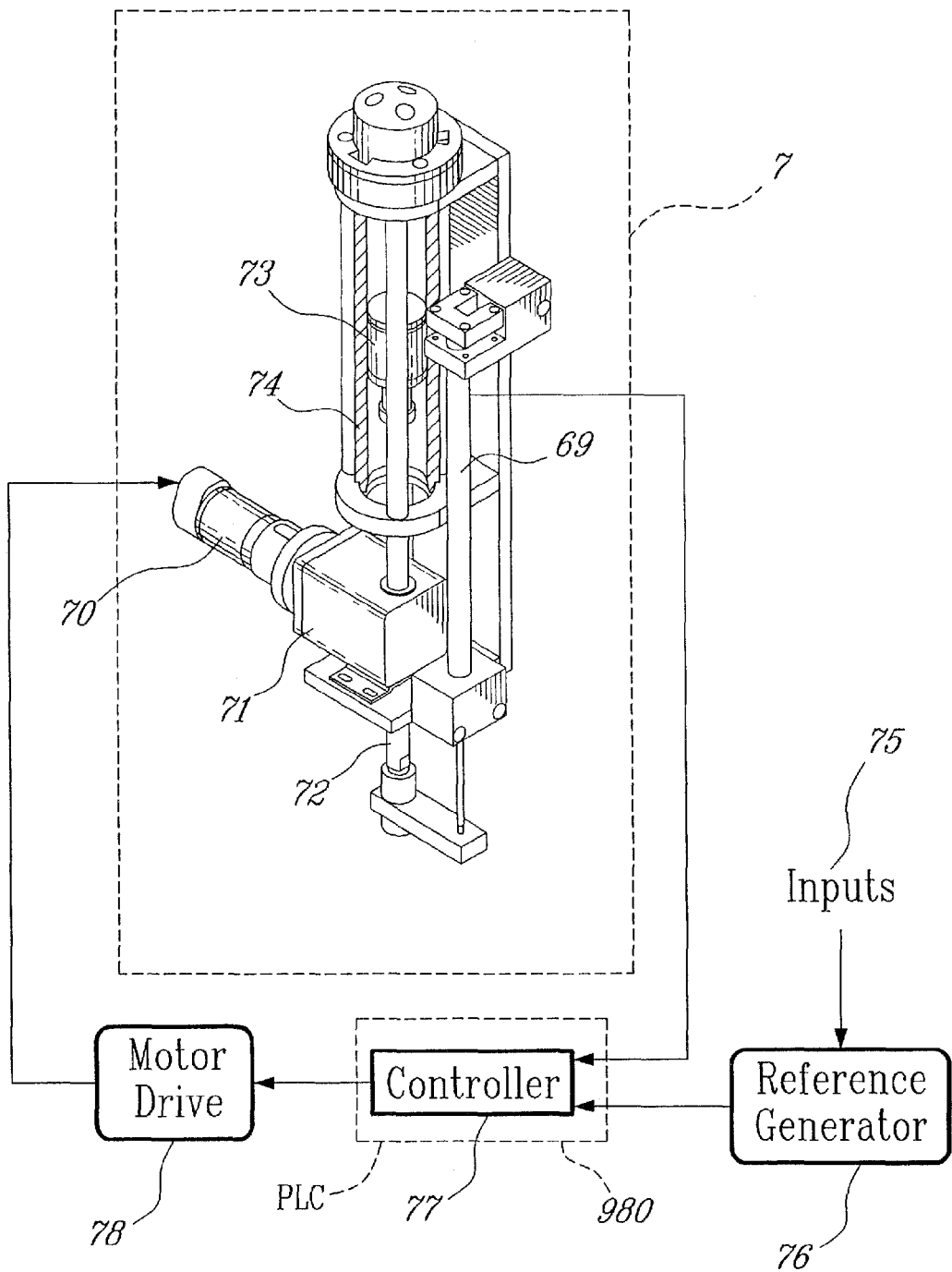
FIG. 10 is an isometric view of one example of a piston pump, with a schematic block diagram describing monitoring and control of the position of the piston of the pump.
Figure 11:
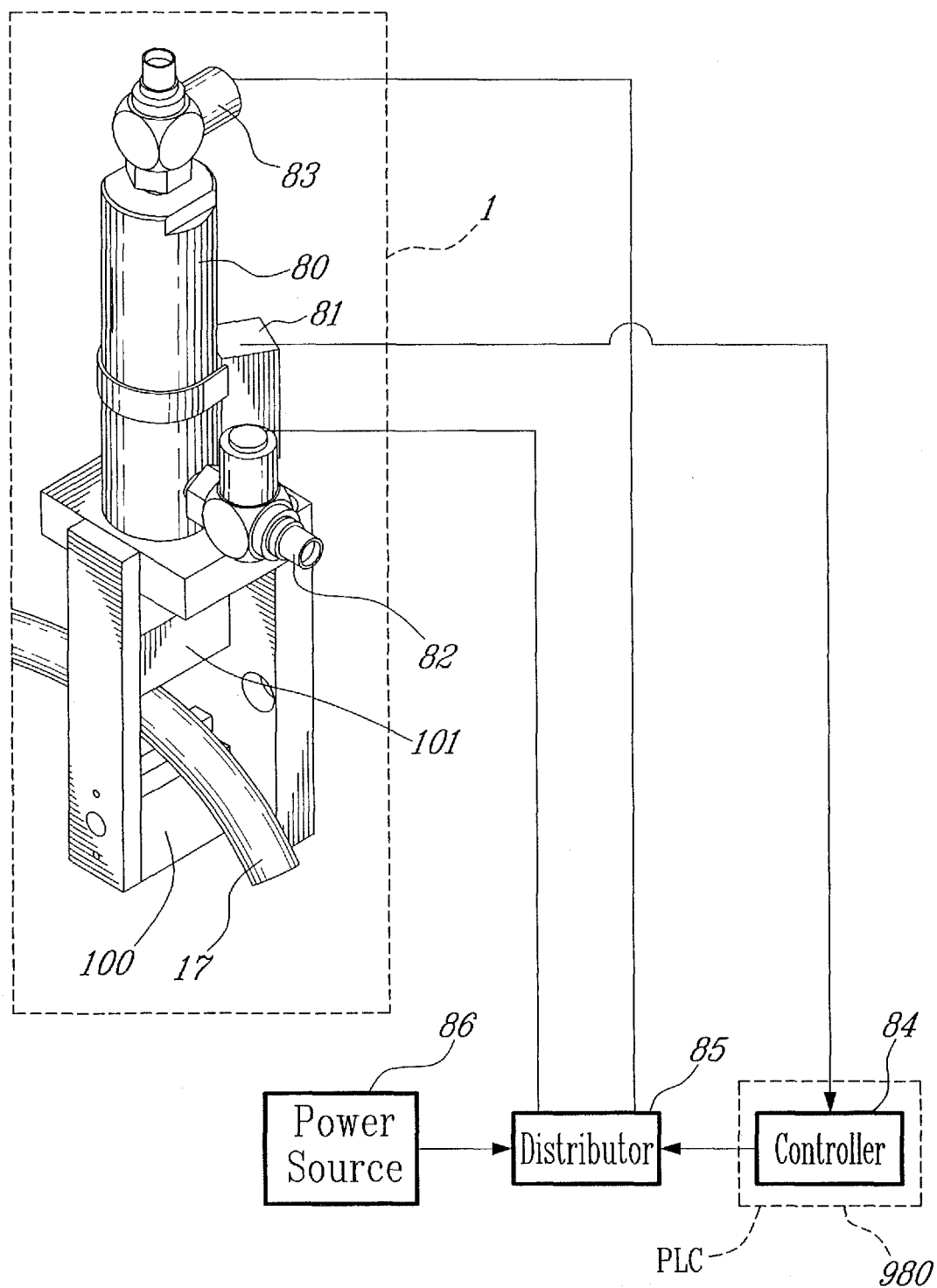
FIG. 11 is an isometric view of one example of a pinch valve, with a schematic block diagram describing monitoring and control of the position of the pinch valve.

Pumps 7 and 8 respectively inject and withdraw predetermined quantities of PFC liquid into and from the patient's lungs in accordance with parameters entered by the health-care personnel on the control panel (for example touch panel 970 of FIG. 12). In the non-restrictive illustrative embodiment of the total liquid ventilator system, the expiration pump 8 is a mirror image of the inspiration pump 7. Therefore, the overall structure and operation of both pumps 7 and 8 will be described in relation to pump 7. FIG. 10 illustrates the structure of pump 7.

Inspiration pump 7 comprises an electric motor 70 mounted on a gearbox 71. The function of the gearbox is to convert the rotational movement of the electric motor 70 to a translation movement. The gearbox 71 thus displaces a shaft 72 along an axis, which in turn displaces the piston 73 in a cylinder 74 along the same axis. Axial movement of the piston 73 will expel from or draw PFC liquid in the cylinder 74. A linear potentiometer 69, mounted on shaft 72 of gearbox 71, indicates the position of the piston 73 within the cylinder 74. Obviously, the linear potentiometer 69 can be replaced by any other suitable sensor capable of producing a measurement indicative of the position of piston 73 within the cylinder 74.

Depending on the weight of the patient, the diameter of the piston 73 and cylinder 74 can be increased in order to increase the volume of liquid displaced by a piston stroke, while maintaining or increasing the length of the cylinder 74 and hence the length of the stroke of the piston 73. The pump cylinder 74 can be made either of an opaque or transparent material.

FIG. 10 further illustrates a controller 77 forming part of PLC 980 of FIG. 12 and whose task is to control injection or withdrawal, with precision, of a volume of PFC liquid determined by the health-care personnel and entered through the control panel (for example touch panel 970 of FIG. 12). To achieve this function, the position of the piston 73 measured by the linear potentiometer 69 is compared to a position reference 76 by the controller 77. This position reference may be modified in accordance with various parameters 75, such as the volume of PFC liquid to be injection or withdrawn from the patient's lungs, the profile of liquid injection or withdrawal, etc. These parameters are entered on the control panel (for example touch panel 970 of FIG. 12) by the health-care personnel. The position reference may take the form of a sinusoidal curve, a ramp, an exponential curve and so on and has a variable time axis. The result of this comparison is then transmitted to a motor drive (power amplifier) 78, which adjusts the speed of the motor 70 as well as the duration of operation of this motor.

The diameter of the piston 73 can be adjusted as a function of the weight of the patient. The diameter shown is suitable for newborns or infants smaller than 9 kg. By doubling the piston diameter, a child of a weight up to 36 kg can be ventilated, and by tripling the diameter, an adult up to a weight of 81 kg can be ventilated.

Position control of the pump pistons as well as independent control of the motor drives enables the implementation of complex ventilation profiles, which otherwise would not be possible.

Valve System

Elements 1, 2, 3 and 4 of FIG. 1 are pinch valves. The criteria motivating this choice are low valve dead-volume, available mechanical force and ease of sterilization. An advantage is that the valves do not need to be sterilized between each use of the total liquid ventilator system; only the flexible tube is changed. Of course, to carry out the overall concept, other types of valves capable of performing the same duty could be used.

A pinch valve requires a pneumatic cylinder 80 (FIG. 11) to pinch a flexible tube 17 crossing it, thus blocking liquid flow. Flow regulators 82 and 83 are used to set a delay of valve opening and closure and thereby avoid pressure peaks in the liquid circuit. A sensor 81 mounted on the body of the pneumatic cylinder 80 indicates to a controller 84 forming par of the PLC 980 of FIG. 12 that the valve is closed. The controller 84 commands the opening and closing of the valve by sending a command to a gas distributor 85 interposed between a pneumatic source 86 and the flow regulators 82 and 83.

Suitable tubing sizes in the valves may range from very small to ¾ inch. If the use of tubes greater than ¾ inch in diameter is required, the distance between parts 100 and 101 and the length of the stroke of the pneumatic cylinder 80 may simply be increased.

Controller

Figure 13:
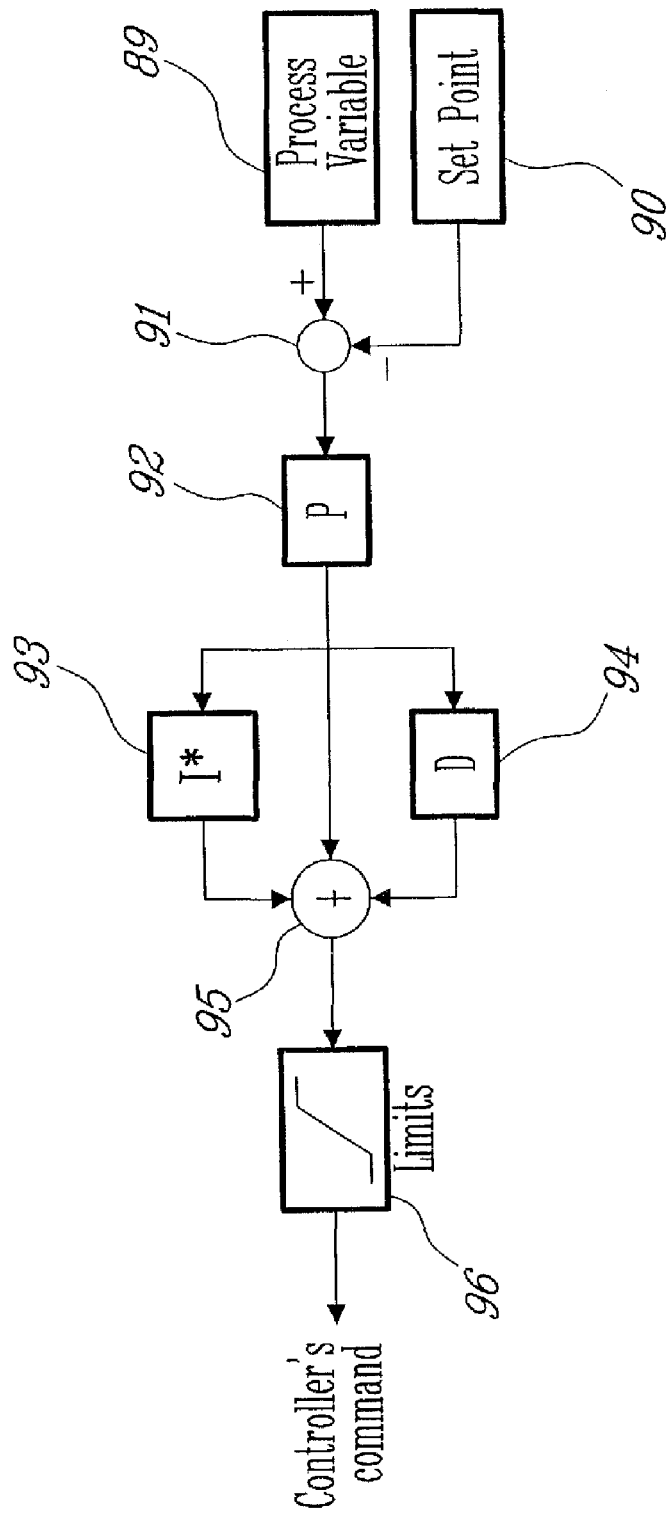
FIG. 13 is a schematic block diagram of one example of a typical PLC used to control the pumping, heating and condensation components.

The typical programmable controller (PLC) used for the heating, pumping and condensation systems is shown in FIG. 13. The process variable 89 is compared to a reference 90. The difference 91 between the values 89 and 90 is then multiplied by proportional 92, integral 93 and derivative 94 gains. The result of each product is then summed by an adder 95 to obtain a command signal. This command signal is then sent to the system to be controlled.

A saturation block 96 limits the command signal within a predefined range of analog values. To avoid the problems related to the imposition of such saturation, integrator 93 must be provided with anti wind-up.

Advantages

A first advantage resides in the modularity of the oxygenators, permitting adjustment of the total liquid ventilation system to the weight of the patient. The interest of an infant oxygenator module resides in its optimization for a PFC liquid flow rate corresponding to a 9 kg patient (current prototype). With two (2) and four (4) infant modules in parallel, the total liquid ventilator system is capable of ventilating 18 and 36 kg patients, respectively. For adults, a single oxygenator module having twice the gas exchange surface area of the infant module is sufficient for 36 kg of body mass load. Thus with three (3) adult modules, the device can ventilate a patient weighing up to 108 kg.

Another advantage comes from the pumping system with independently controlled pumps and an instrumented buffer reservoir. This configuration allows precise estimation of the total volume of PFC liquid in the ventilator system and therefore determination of the volume of PFC liquid in the lungs of the patient by deduction. It also allows optimizing of the time of residence of the PFC liquid in the oxygenator, modifying and/or correcting lung volume during ventilation, and planning of variable ventilation profiles. Finally, it allows the clinician to modulate and optimize gas exchange thanks to an easily accessible and effective user/machine interface.

Thus, until now, total liquid ventilator systems have resulted from the assembly of sundry components: a pump, a heating system, a control unit, a condenser and an oxygenator. Although the combination of these components could provide acceptable results for the total liquid ventilation of newborns, which requires processing of low flow rates of PFC liquid, it runs into difficulties when practising total liquid ventilation of adults, for which flow rates ten times higher may be required. The non-restrictive illustrative embodiment of the present invention responds to this problem by integrating the condenser and the heating element into that which is called a modular oxygenator. By modularity is meant that the oxygenator can be joined in series or in parallel with other oxygenators in order to process large quantities of PFC liquid without having to re-size them. In addition, the independent control of the two pumps as well as the measurement of the quantity of PFC liquid in the ventilation system enables estimation at all times of the volume of PFC liquid contained in the patient's lungs and to correct the residual volume (the volume of PFC liquid remaining in the lungs at the end of expiration).

Although the present invention has been disclosed in the foregoing description in connection with a non-restrictive illustrative embodiment thereof, this embodiment can be modified at will, within the scope of the appended claims, without departing from the spirit and nature of the present invention.

What is claimed is:

1. A method of applying total liquid ventilation to a patient according to a ventilation cycle including inspiration and expiration profiles, comprising:
   supplying oxygenated liquid to the lungs of the patient during inspiration, wherein supplying oxygenated liquid to the patient's lungs comprises accumulating oxygenated liquid from an oxygenator unit in an inspiration piston pump during expiration, and transferring the oxygenated liquid accumulated in the inspiration piston pump to the patient's lungs during inspiration;
   withdrawing liquid from the patient's lungs during expiration, wherein withdrawing liquid from the patient's lungs comprises accumulating liquid from the patient's lungs in an expiration piston pump during expiration, and transferring the liquid accumulated in the expiration piston pump directly to the oxygenator unit during inspiration; and
   controlling independently supply of oxygenated liquid to the patient's lungs and withdrawal of liquid from the patient's lungs, the supply and withdrawal independent control comprising producing a ventilation cycle having independently controlled inspiration and expiration profiles.

2. A method of applying total liquid ventilation as defined in claim 1, further comprising:
   simultaneously starting transfer of the oxygenated liquid accumulated in the inspiration piston pump to the patient's lungs and transfer of the liquid accumulated in the expiration piston pump to the oxygenator unit; and
   extending a time of residence of the liquid in the oxygenator unit by transferring the liquid accumulated in the expiration piston pump to the oxygenator unit more rapidly than the oxygenated liquid accumulated in the inspiration piston pump is transferred to the patient's lungs.

3. A method of applying total liquid ventilation as defined in claim 1, further comprising:
   producing a pause between (a) transfer of the oxygenated liquid accumulated in the inspiration piston pump to the patient's lungs and transfer of the liquid accumulated in the expiration piston pump to the oxygenator unit, and (b) accumulation of oxygenated liquid from the oxygenator unit in the inspiration piston pump and accumulation of liquid from the patient's lungs in the expiration piston pump.

4. A method of applying total liquid ventilation as defined in claim 1, further comprising:
   producing a pause between (a) accumulation of oxygenated liquid from the oxygenator unit in the inspiration piston pump and accumulation of liquid from the patient's lungs in the expiration piston pump, and (b) transfer of the oxygenated liquid accumulated in the inspiration piston pump to the patient's lungs and transfer of the liquid accumulated in the expiration piston pump to the oxygenator unit.

5. A method of applying total liquid ventilation as defined in claim 1, further comprising:
   starting accumulation of liquid from the patient's lungs in the expiration piston pump before accumulation of oxygenated liquid from the oxygenator unit in the inspiration piston pump, and simultaneously ending accumulation of oxygenated liquid from the oxygenator unit in the inspiration piston pump, and accumulation of liquid from the patient's lungs in the expiration piston pump.

6. A system for applying total liquid ventilation to a patient according to a ventilation cycle including inspiration and expiration profiles, comprising:

- an inspiration pump for supplying oxygenated liquid to the lungs of the patient, wherein the inspiration pump comprises an inspiration piston pump for accumulating oxygenated liquid from the oxygenator during expiration, and for subsequently transferring the accumulated oxygenated liquid to the patient's lungs during inspiration; and
- an expiration pump for withdrawing liquid from the patient's lungs, wherein the expiration pump comprises an expiration piston pump for accumulating liquid from the patient's lungs during expiration, and for subsequently transferring the liquid accumulated from the patient's lungs directly to the oxygenator during inspiration; and
- a ventilation cycle control means comprising first and second pump controllers connected to the inspiration and expiration pumps, respectively, to control independently said inspiration and expiration pumps in order to produce a ventilation cycle having independently controlled inspiration and expiration profiles.

7. A system for applying total liquid ventilation as defined in claim 6, wherein the first and second pump controllers comprise:

- means for simultaneously starting transfer of the oxygenated liquid accumulated in the inspiration piston pump to the patient's lungs and transfer of the liquid accumulated in the expiration piston pump to the oxygenator unit; and
- means for extending a time of residence of the liquid in the oxygenator unit by transferring the liquid accumulated in the expiration piston pump to the oxygenator unit more rapidly than the oxygenated liquid accumulated in the inspiration piston pump is transferred to the patient's lungs.

8. A system for applying total liquid ventilation as defined in claim 6, wherein the first and second pump controllers comprise:

- means for producing a pause between (a) transfer of the oxygenated liquid accumulated in the inspiration piston pump to the patient's lungs and transfer of the liquid accumulated in the expiration piston pump to the oxygenator unit, and (b) accumulation of oxygenated liquid from the oxygenator unit in the inspiration piston pump and accumulation of liquid from the patient's lungs in the expiration piston pump.

9. A system for applying total liquid ventilation as defined in claim 6, wherein the first and second pump controllers comprise:

- means for producing a pause between (a) accumulation of oxygenated liquid from the oxygenator unit in the inspiration piston pump and accumulation of liquid from the patient's lungs in the expiration piston pump, and (b) transfer of the oxygenated liquid accumulated in the inspiration piston pump to the patient's lungs and transfer of the liquid accumulated in the expiration piston pump to the oxygenator unit.

10. A system for applying total liquid ventilation as defined in claim 6, wherein the first and second pump controllers comprise:

- means for starting accumulation of liquid from the patient's lungs in the expiration piston pump before accumulation of oxygenated liquid from the oxygenator unit in the inspiration piston pump, and
- means for simultaneously ending accumulation of oxygenated liquid from the oxygenator unit in the inspiration piston pump, and accumulation of liquid from the patient's lungs in the expiration piston pump.

* * * * *